US011311573B2

(12) United States Patent
Celiker

(10) Patent No.: US 11,311,573 B2
(45) Date of Patent: *Apr. 26, 2022

(54) PHARMACEUTICAL PREPARATIONS AND METHODS TO MANAGE WEIGHT AND TO MODULATE THE GUT MICROBIOTA

(71) Applicant: XENO BIOSCIENCES INC., Somerville, MA (US)

(72) Inventor: Hasan Celiker, Somerville, MA (US)

(73) Assignee: Xeno Biosciences Inc., Somerville, MA (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/465,146

(22) PCT Filed: Nov. 29, 2017

(86) PCT No.: PCT/US2017/063809
§ 371 (c)(1),
(2) Date: May 29, 2019

(87) PCT Pub. No.: WO2018/102469
PCT Pub. Date: Jun. 7, 2018

(65) Prior Publication Data
US 2020/0078397 A1 Mar. 12, 2020

Related U.S. Application Data

(60) Provisional application No. 62/428,319, filed on Nov. 30, 2016.

(51) Int. Cl.
*A61K 33/40* (2006.01)
*A61P 3/04* (2006.01)
*A61K 9/50* (2006.01)
*A61K 31/327* (2006.01)
*A61K 38/44* (2006.01)

(52) U.S. Cl.
CPC ............ *A61K 33/40* (2013.01); *A61K 9/5026* (2013.01); *A61K 9/5047* (2013.01); *A61K 31/327* (2013.01); *A61K 38/44* (2013.01); *A61P 3/04* (2018.01)

(58) Field of Classification Search
CPC .... A61K 33/40; A61K 31/327; A61K 9/4891; A61K 9/0053; A61P 3/00; A61P 3/04
See application file for complete search history.

(56) References Cited

U.S. PATENT DOCUMENTS

| 5,000,869 | A | * | 3/1991 | Dittert | ................. | C11D 3/3955 |
| | | | | | | 252/186.34 |
| 5,759,539 | A | | 6/1998 | Whitmire | | |
| 9,855,294 | B2 | | 1/2018 | Heshmati et al. | | |
| 10,945,974 | B2 | * | 3/2021 | Celiker | ................ | A61K 9/4891 |
| 11,179,356 | B2 | | 11/2021 | Celiker | | |
| 11,179,357 | B2 | | 11/2021 | Celiker | | |
| 2004/0146467 | A1 | | 7/2004 | Pellico | | |
| 2005/0008584 | A1 | | 1/2005 | Montgomery | | |
| 2006/0110451 | A1 | | 5/2006 | Lin et al. | | |
| 2006/0193794 | A1 | | 8/2006 | Kim et al. | | |
| 2006/0270655 | A1 | | 11/2006 | Swick et al. | | |
| 2009/0169630 | A1 | | 7/2009 | Ward et al. | | |
| 2010/0092550 | A1 | | 4/2010 | Cabral | | |
| 2010/0172874 | A1 | | 7/2010 | Turnbaugh et al. | | |
| 2011/0002986 | A1 | | 1/2011 | Durig et al. | | |
| 2012/0052151 | A1 | | 3/2012 | Sannino et al. | | |
| 2012/0058094 | A1 | | 3/2012 | Blaser et al. | | |
| 2013/0012590 | A1 | | 1/2013 | Zadini et al. | | |
| 2013/0195830 | A1 | | 8/2013 | Sipka et al. | | |
| 2013/0295525 | A1 | | 11/2013 | Sagel | | |
| 2014/0212492 | A1 | | 7/2014 | Mateescu et al. | | |
| 2015/0125525 | A1 | * | 5/2015 | Bravo Gonzalez | .... | A61K 9/284 |
| | | | | | | 424/472 |
| 2018/0147167 | A1 | | 5/2018 | Celiker | | |
| 2021/0161839 | A1 | | 6/2021 | Celiker | | |
| 2021/0169829 | A1 | | 6/2021 | Celiker | | |
| 2021/0177784 | A1 | | 6/2021 | Celiker | | |

FOREIGN PATENT DOCUMENTS

| CN | 107921073 A | 4/2018 | |
| JP | 2005336072 A | * 12/2005 | |
| WO | WO-9217400 A1 | * 10/1992 | ........... C01B 15/106 |
| WO | WO-96/39174 A1 | 12/1996 | |
| WO | WO-2007/134304 A1 | 11/2007 | |
| WO | WO-2008/076696 A2 | 6/2008 | |
| WO | WO-2010/101844 A1 | 9/2010 | |

(Continued)

OTHER PUBLICATIONS

WO-9217400-A1 (Espacenet English translation, downloaded Mar. 2021) (Year: 2021).*

(Continued)

*Primary Examiner* — Mark V Stevens

(74) *Attorney, Agent, or Firm* — Choate, Hall & Stewart LLP; Brenda Herschbach Jarrell; David E. Shore

(57) ABSTRACT

A pharmaceutical preparation, comprising: A) A plurality of particles, each particle comprising: 1) a core comprising at least one agent that increases oxygen tension and/or redox potential and/or pH in the colon of a subject following administration to the subject, and 2) an enteric coating encasing the core; and B) a capsule or sachet encasing the plurality of particles. Methods of weight management for a subject, comprising administering the pharmaceutical preparation to a subject in need thereof.

43 Claims, 5 Drawing Sheets

(56) References Cited

FOREIGN PATENT DOCUMENTS

| | | | |
|---|---|---|---|
| WO | WO-2010/134827 A1 | 11/2010 | |
| WO | WO-2013/093877 A2 | 6/2013 | |
| WO | WO-2013/103919 A2 | 7/2013 | |
| WO | WO-2013/130773 A2 | 9/2013 | |
| WO | WO-2014/046804 A1 | 3/2014 | |
| WO | WO-2015/000053 A1 | 1/2015 | |
| WO | WO-2015000053 A1 * | 1/2015 | ............... A61P 1/14 |
| WO | WO-2016/094218 A1 | 6/2016 | |
| WO | WO-2016/172658 A2 | 10/2016 | |
| WO | WO-2016/196440 A1 | 12/2016 | |
| WO | WO-2017/174744 A1 | 10/2017 | |
| WO | WO-2018/102469 A1 | 6/2018 | |
| WO | WO-2018/203083 A2 | 11/2018 | |
| WO | WO-2019/037682 A1 | 2/2019 | |

OTHER PUBLICATIONS

JP-2005336072-A (Espacenet English translation, downloaded Mar. 2021) (Year: 2021).*

Abdeen, G. and Le Roux, C., Mechanism Underlying the Weight Loss and Complications of Roux-en-Y Gastric Bypass. Review, Obes Surg, 26:410-421 (2016).

Arble, D. et al., Mechanisms underlying weight loss and metabolic improvements in rodent models of bariatric surgery, Diabetologia, 58(2):211-220 (2015).

Berberine and Its Many Benefits, Feb. 24, 2018, accessed on Dec. 7, 2018, at https://enzymedica.com/blogs/naturaldigestivehealth/berberine-and-its-many-benefits, 7 pages.

Calinescu, C. et al., Carboxymethyl starch: Chitosan monolithic matrices containing diamine oxidase and catalase for intestinal delivery, International Journal of Pharmaceutics, 428:48-56 (2012).

Catalase Supplement, accessed on Dec. 7, 2018, at https://shop.suzycohen.com/products/catalase, 5 pages.

Catalase, How Catalase Works, May 2, 2015 (May 2, 2015), XP002787111, Retrieved from the Internet: URL:https://www.ebi.ac.uk/interpro/potm/2004 9/Page2.htm [retrieved on Dec. 5, 2018], 2 pages.

Chambers, E. et al., Effects of targeted delivery of propionate to the human colon on appetite regulation, body weight maintenance and adiposity in overweight adults, Gut, 64:1744-1754 (2015).

Damms-Machado, A. et al., Effects of Surgical and Dietary Weight Loss Therapy for Obesity on Gut Microbiota Composition and Nutrient Absorption, Hindawi Publishing Corporation, BioMed Research International, 2015, Article ID 806248,12 pages (2014).

European Search Report, Application No. 16804207.5, dated Jan. 24, 2019.

Graessler, J. et al., Metagenomic sequencing of the human gut microbiome before and after bariatric surgery in obese atienls with type 2 diabetes: correlalin with inflammatory and metabolic parameters, The Pharmacogenomics Journal, 13:514-522 (2013).

Hartman, A. et al., Human gut microbiome adopts an alternative state following small bowel transplantation, PNAS, 106(40):17187-17192 (2009).

Homozon web page, "http://hello-earth.com/homozon/listen/georgefreibotthomozon17march2011.html," accessed Sep. 7, 2018, 14 pages.

Ilhan, Zehra Esra, Microbiome Aller Bariatric Surgery and Microbial Insights into Surgical Weight Loss, Dissertation, Arizona State University, 2220 pages (2016).

International Search Report and Written Opinion for Application No. PCT/US16/34973, dated Sep. 9, 2016 (12 pages).

International Search Report and Written Opinion for Application No. PCT/US17/63809, dated Feb. 6, 2018 (8 pages).

Jogender, K. et al., Efficacy, Safety, and Tolerability Evaluation of Global Healing Center's Oxy Powder® in Treating Irritable Bowel Syndrome {Constipation— Predominant) IBS-C), International Journal of Pharma and Bio Sciences, 1(2): 14 pages (2010).

John, G. K. et al., Dietary Alteration of the Gut Microbiome and Its Impact on Weight and Fat Mass: A Systematic Review and Meta-Analysis, Genes, 9:167, 19 pages (2018).

Ley, R. et al., Human gut microbes associated with obesity, Nature, 444:1022-23 (2006).

Ley, R. et al., Obesity alters gut microbial ecology, PNAS, 102(31):11070-75 (2005).

Li, J. et al., Metabolic surgery profoundly influences gut microbialehost metabolic cross-talk, Gut, 60:1214-1223 (2011).

Liou, A. et al., Conserved Shifts in the Gut Microbiola Due to Gastric Bypass Reduce Host Weight and Adiposity, Sci Transl Med, 5(178), 178ra41, 12 pages (2013).

MagO7 Product Information Guide, accessed on Dec. 7, 2018, at https://www.dropbox.com/s/1t58btqm5wqu0qb/ EONARD_mag07_90ct_2018.pdf?dl=0, 3 pages.

Nutritional Brands—MagO7, available at http://www.nbpure.US/mago7/, accessed Aug. 8, 2018, 11 pages.

Peat, C. et al., The Intestinal Microbiome in Barialric Surgery Patients, Eur Eal Disord Rev, 23(6):496-503 (2015).

Ryan, K. et al., FXR is a molecular target for the effects of vertical sleeve gastrectomy, Nature, 509:183-190 (2014).

Saeidi, N. et al., Reprogramming of Intestinal Glucose Metabolism and Glycemic Control in Rais After Gastric Bypass, Science, 341:406-410 (2013).

Seeley, R. et al., The Role of Gut Adaptation in the Potent Effects of Multiple Barialric Surgeries on Obesity nd Diabetes, Cell Metabolism, 21:369-378 (2015).

Sun, H. et al., Modulation of Microbiota-Gut-Brain Axis by Berberine Resulting in Improved Metabolic Status in High-Fat Diet-Fed Rats, Obesity Facts, 9:356-378 (2016).

The steps I took to lose weight, Internet, May 122, 2015 (May 12, 2015), XP002787110, Retrieved from the Internet: URL:https://web.archive.org/web/20150512104604/http:/imyplace.frontier.com/-felipe2/id26.html [retrieved on Dec. 5, 2018] 4 pages.

Thread: My experience of taking Hydrogen Peroxide 35% food grade, diluted in water, Jun. 1, 2014, accessed Dec. 7, 2018, at http://projectavalon.net/forum4/showthread.php771893-My-experience--0f-taking-Hydrogen- Deroxide-35-food-grade-diluted-in-water, 15 pages.

Turnbaugh, P. et al., A core gut microbiome in obese and lean twins, Nature, 457(7228):180-484 (2009).

Ward, K. R. et al., Chemical Oxygen Generation, Resperatory Care, 58(1):184-195 (2013).

Your Top Oxy Powder Frequently Asked Questions Answered, available at https://thewellbeingclinic.ie/oxypowder/ Jxypowder-frequently-asked-questions/, accessed on Dec. 7, 2018, 9 pages.

Zhang, H. et al., Human gut microbiota in obesity and after gastric bypass, PNAS, 106(7):2365-2370 (2009).

Zhang, K. et al., Modulation of gut microbiota by berberine and metformin during the treatment of high-fat diet-induced obesity in rats, Scientific Reports, 5:14405, 10 pages (2015).

Chambers, AP et al., Weight-independent changes in blood glucose homeostasis after gastric bypass or vertical sleeve gastrectomy in rats, Gastroenterology, 141:950-8 (2011).

Ciangura, C. et al., Dynamics of change in total and regional body composition after gastric bypass in obese patients, Obesity (Silver Spring), 18:760-5 (2010).

Crowe, T.C., Safety of low-carbohydrate diets, Obes Rev, 6:235-45 (2005).

Flint, A. et al., Reproducibility, power and validity of visual analogue scales in assessment of appetite sensations in single test meal studies, Int. J Obes. Relat. Metab. Disord, 24:38-48 (2000).

Foster, D.W. and McGarry, J.D., The regulation of ketogenesis, Ciba Found Symp., 87:120-31 (1982).

Friedrich, N. et al., Short-term changes of the urine metabolome after bariatric surgery, OMICS, 16:612-20 (2012).

Gralka E. et al., Metabolomic fingerprint of severe obesity is dynamically affected by bariatric surgery in a procedure-dependent manner, Am. J Clin. Nutr., 102:1313-22 (2015).

Jensen, M. et al., Insulin regulation of lipolysis in nondiabetic and IDDM subjects, Diabetes, 38:1595-601 (1989).

(56) References Cited

OTHER PUBLICATIONS

Mor, A. et al., Weight loss at first postoperative visit predicts long-term outcome of Roux-en-Y gastric bypass using Duke weight loss surgery chart, Surg Obes Relat Dis, 8:556-60 (2012).
Palaniappan, L.P., Heterogeneity in the Relationship Between Ethnicity, BMI, and Fasting Insulin, Diabetes Care, 25 (2002).
Quintero, P. et al., Impact of oxygen availability on body weight management, Medical Hypotheses, 74:901-907 (2010).
Savendahl, L. and Underwood, L. E., Fasting increases serum total cholesterol, LDL cholesterol and apolipoprotein Bin healthy, nonobese humans, J Nutr., 129:2005-8 (1999).
Sodium Percarbonate SIDS Initial Assessment Profile, In Organisation for Economic Co-operation and Development Existing Chemicals Database, retrieved from https://hpvchemicals.oecd.org/ui/handler.axd?id=ab75c996-6905-4195-9e2c-5abd5e465d5b, 3 pages (2005).
Swaner, J.C., and Connor, W. E., Hypercholesterolemia of total starvation: its mechanism via tissue mobilization of cholesterol, Am. J Physiol., 229:365-9 (1975).
Wickremesekera, K. et al., Loss of insulin resistance after Roux-en-Y gastric bypass surgery: a time course study, Obes Surg, 15:474-81 (2005).
Xue, J. and Zhang, Z., Preparation and characterization of calcium-shellac spheres as a carrier of carbamide peroxide, Journal of Microencapsulation, 25(8):523-530 (2008).
Extended European Search Report, Application No. 21186265.1, dated Oct. 26, 2021.
The steps I took to lose weight, INTERNET, 122 May 2015 (May 12, 2015), XP002787110, Retrieved from the Internet: URL:https://web.archive.org/web/20150512104604/http:/imyplace.fro ntier.com/-felipe2/id26.html [retrieved on May 12, 2018] 4 pages.

\* cited by examiner

PHARMACEUTICAL PREPARATIONS AND METHODS TO MANAGE WEIGHT AND TO MODULATE THE GUT MICROBIOTA

With only diet, exercise, and bariatric surgery as options, the lack of effective and safe medications for treating metabolic disorders and diseases (such as obesity), metabolic syndrome, and cardiovascular disease are significant unmet medical needs. For example, obesity is a life-threatening disorder in which there is an increased risk of morbidity and mortality arising from concomitant diseases such as type II diabetes, hypertension, obstructive sleep apnea, inflammation, stroke, cancer and gallbladder disease. Obesity is now a major healthcare issue in the Western World and increasingly in some third world countries. Currently about 35% of the population of the USA is now considered obese and an additional ~40% overweight. Management of body weight and body mass index (BMI) is also correlated with many indicators of health and even a numerically small reduction of body weight can lead to a profound improvement in obesity related conditions and increase quality of life and life expectancy.

Microbiome targeted therapeutics have a potential to address this problem, as it is becoming increasingly clear that the gut microbiota has a causal role in alleviating or mediating metabolic disorders, including obesity. However, microbiome modulation approaches to date have predominantly focused on utilizing probiotics, prebiotics, antibiotics or fecal transplants, which lack targeted or broad-spectrum efficacy and may have unfavorable safety and efficacy profiles. Accordingly, there is a need for new methods and compositions for managing the weight of a subject and/or treating metabolic disorders including obesity, metabolic syndrome, and cardiovascular disease. The inventions disclosed herein meet these and other needs.

SUMMARY

The inventor has discovered that administering an effective amount to the small intestine and/or large intestine of a subject of at least one agent that increases oxygen tension and/or redox potential and/or pH in the colon of the subject has a beneficial effect on the gut microbiome of the subject. By increasing the oxygen tension and/or redox potential and/or pH the colon environment is modified such that (1) the relative abundance of bacterial types known to promote at least one condition selected from a metabolic disease or disorder (such as obesity), metabolic syndrome, and cardiovascular disease is reduced; and/or (2) the relative abundance of bacterial types known to ameliorate at least one condition selected from a metabolic disease or disorder (such as obesity), metabolic syndrome, and cardiovascular disease is increased. Modulation in this way provides a means to manage the weight of a subject. See for example co-pending International Application No. PCT/US2016/034973, filed 31 May 2016.

This invention specifically provides improved pharmaceutical preparations for delivering the at least one agent that increases oxygen tension and/or redox potential and/or pH in the colon of a subject to the target area within the gastrointestinal tract of the subject. The inventor has found that a multiparticulate pharmaceutical preparation in which each particle is enteric coated and then the particles are encased in a capsule or sachet for administration to a subject provides a desirable means of delivering the at least one agent that increases oxygen tension and/or redox potential and/or pH in the colon of a subject to the target area within the gastrointestinal tract of the subject. In several embodiments this formulation exhibits advantages relative to alternatives in which an entire dose of the agent is encased in a enteric coating (for example as an enteric coated tablet or an enteric coated capsule (in which the enteric coating is on the outside of the capsule).

For example capsules are hard to coat reliably with enteric coating. If coating thickness is too low, then the capsules fail to reliably show enteric properties (they open in acidic conditions). This is due to a failure point at the capsule junction where the body and the cap of the capsule connect. A thin layer of coating sometimes fails to coat over this gap causing failure.

On the other hand, if the coating thickness is increased, it is possible to apply a large amount of polymer over this gap to coat it more reliably. However, unfortunately, a high coating thickness also leads to a non-functional formulation, because the capsules fail to open and release API in vivo. A thick coating layer fails to dissolve in time to open before reaching the colon.

In certain formulations of the invention small round spherical particles of active agent are coated, for example using a fluidized bed. This approach allows coating of particles with smooth surfaces and mitigates any coating failure due to irregularities on the surface (such as a cap-body junction of capsule). This further enables a low enough coating thickness such that the formulation is both acid resistant and opens rapidly once the correct pH is reached in the distal small intestine.

In certain embodiments this approach also provides one or more of the following advantages: Particles spread uniformly over the GI tract, which decrease local concentration of API in the intestines and create a sustained delivery of API to the proximal colon over 3-5 hours; and lower local concentration of API helps reducing any GI irritation or side effects.

Accordingly, in a first aspect this invention provides pharmaceutical preparations comprising a plurality of particles, each particle comprising: 1) a core comprising at least one agent that increases oxygen tension and/or redox potential and/or pH in the colon of a subject following administration to the subject, and 2) an enteric coating encasing the core.

In some embodiments the pharmaceutical preparation is a unit dosage form. In some embodiments the unit dosage form consists of a known number of particles.

In some embodiments the pharmaceutical preparations comprise a plurality of particles and a capsule or sachet encasing the plurality of particles. In some embodiments the pharmaceutical preparation comprises: A) A plurality of particles, each particle comprising: 1) a core comprising at least one agent that increases oxygen tension and/or redox potential and/or pH in the colon of a subject following administration to the subject, and 2) a delayed release coating encasing the core; and B) a capsule or sachet encasing the plurality of particles.

In some embodiments the at least one agent is selected from carbamide peroxide and sodium percarbonate. In some embodiments the at least one agent is sodium percarbonate. In some embodiments the core comprises catalase. In some embodiments the particles further comprise a release rate modifier. In some embodiments the core of the particles comprises the release rate modifier. In some embodiments the particles further comprise a subcoat layer that encases the core and is disposed between the core and the delayed release coating. In some embodiments the subcoat layer comprises HPMC In some embodiments the weight ratio of delayed release coating to core of the particles is from 5% to 50%. In some embodiments the weight ratio of delayed release coating to core of the particles is from 20% to 30%. In some embodiments the weight ratio of delayed release coating to core of the particles is from 30% to 40%. In some embodiments the weight ratio of delayed release coating to core of the particles is from 40% to 50%.

In some embodiments the delayed release coating is an enteric coating that is protective at pH below 5.5. In some embodiments the enteric coating is protective at pH below 6.5. In some embodiments the enteric coating is protective at pH below 7.0. In some embodiments the enteric is protective at pH below 7.4. In some embodiments the delayed release coating is Eudagrit FS30D.

In some embodiments, following oral administration of the pharmaceutical preparation to a subject the core is delivered to the distal ileum and/or colon.

In some embodiments the cores of the plurality of particles have a maximum dimension of from 0.1 to 2 mm. In some embodiments the cores of the plurality of particles have a maximum dimension of from 0.2 to 1.0 mm. In some embodiments the plurality of particles have a maximum dimension of 3.0 mm or less.

In some embodiments the pharmaceutical preparation is provided in a unit dosage form comprising from 25 to 500 mg of the at least one agent. In some embodiments the pharmaceutical preparation is provided in a unit dosage form comprising from 50 to 200 mg of the at least one agent.

This invention also provides methods of using the pharmaceutical preparations of the invention for weight management of a subject. In some embodiments the methods comprise administering a pharmaceutical preparation of the invention to the subject. In some embodiments weight management comprises at least one of weight loss, maintenance of weight, controlling weight gain, body mass index (BMI) reduction, maintenance of BMI, and controlling BMI gain. In some embodiments the subject is overweight or obese. In some embodiments the subject has at least one weight-related condition. In some embodiments the at least one weight-related condition is selected from a metabolic disease or disorder, metabolic syndrome, and cardiovascular disease.

In some embodiments administering the pharmaceutical preparation to the subject increases the relative abundance of at least one of aerobic bacteria and facultatively anaerobic bacteria in the microbiota of the colon of the subject by at least 100%. In some embodiments administering the pharmaceutical preparation to the subject increases the relative abundance of bacteria in at least one phylum selected from Proteobacteria, Bacteriodetes, and Verrucomicrobia in the microbiota of the colon of the subject by at least 100%. In some embodiments administering the pharmaceutical preparation to the subject decreases the relative abundance of bacteria in the Firmicutes phylum in the microbiota of the colon of the subject.

In some embodiments the pharmaceutical preparation is administered once a day, twice a day, three times a day, or four times a day. In some embodiments from 50 to 200 mg of the at least one agent is administered at each dosing. In some embodiments the pharmaceutical preparation is administered for a dosing period of at least five days, and wherein the weight of the subject in reduced by at least 2%. In some embodiments the pharmaceutical preparation is administered for a dosing period of at least five days, and wherein the weight of the subject in reduced by at least 5%.

In some embodiments the subject is a human.

In some embodiments administering the pharmaceutical preparation to the subject increases ketone body excretion in the urine of the subject.

This invention also provides methods of increasing ketogenesis by a subject. In some embodiments the methods comprise administering a pharmaceutical preparation of the invention to the subject. This invention also provides uses of a pharmaceutical preparation of the invention to manage the weight of a subject.

This invention also provides uses of a pharmaceutical preparation of the invention for manufacturing a medicament intended to manage the weight of a subject.

This invention also provides uses of a pharmaceutical preparation of the invention to increase ketogenesis by a subject.

This invention also provides uses of a pharmaceutical preparation of the invention for manufacturing a medicament intended to increase ketogenesis by a subject.

DETAILED DESCRIPTION

A. Introduction

Figure 1:
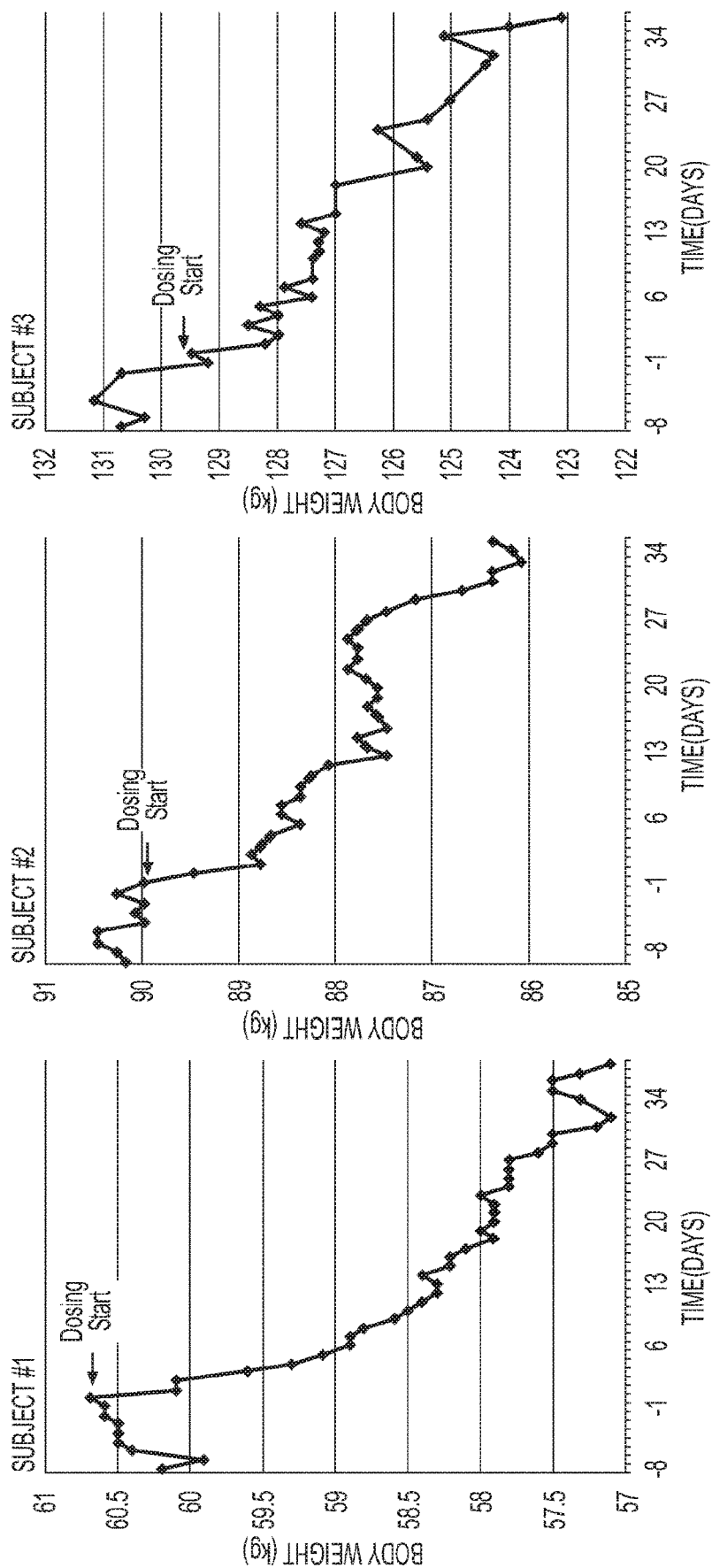
FIG. 1 shows body weight time courses for subjects 1-3.

Bariatric surgical procedures such as vertical sleeve gastrectomy (VSG) and Roux-en-Y gastric bypass (RYGB) are the most potent treatments available to produce sustained reductions in body weight and improvements in glucose regulation. While traditionally these effects are attributed to mechanical aspects of these procedures, such as restriction and malabsorption, a growing body of evidence from mouse models of these procedures points to physiological changes that mediate the potent effects of these surgeries. In particular, there are similar changes in gut hormone secretion, bile acid levels, and composition after both of these procedures. Moreover, loss of function of the nuclear bile acid receptor (FXR) greatly diminishes the effects of VSG. Bariatric surgeries are linked to profound changes in the gut microbiome that also mediate at least some of these surgical effects.

Intestinal microorganisms could be contributing to obesity by increasing recovery of energy from the diet and via the impact of microbial metabolites or microbial cell-derived signals on host pathways that regulate energy homoeostasis and lipid metabolism. Several gut microbial diversity surveys in mouse models [Ley R E, Backhed F, Turnbaugh P, Lozupone C A, Knight R D, Gordon J I. "Obesity alters gut microbial ecology." Proc Natl Acad Sci USA 2005; 102: 11070-11075] and humans [Ley R E, Turnbaugh P J, Klein S, Gordon J I. "Microbial ecology: human gut microbes associated with obesity." Nature 2006; 444: 1022-1023; and Turnbaugh P J, Hamady M, Yatsunenko T, Cantarel B L, Duncan A, Ley R E et al. "A core gut microbiome in obese and lean twins." Nature 2009; 457: 480-484] provided evidence that obesity was associated with a decreased proportion of Bacteroidetes and a higher proportion of Firmicutes. These and other data suggest that the gut microbiome plays a regulatory role in obesity and related metabolic conditions.

To date, efforts to modulate the gut microbiome have focused on strategies to directly add helpful types of bacteria to the gut and/or strategies to reduce harmful types of bacteria in the gut by the use of antibiotics. These approaches are necessarily challenging because added bacteria must compete against endogenous bacteria and antibiotics are often a crude tool that target several types of bacteria at once and there are concerns over antibiotic resistance development. Accordingly, there is a need in the art to provide methods and compositions to modify the gut microbiome in a manner that counters obesity and other metabolic conditions and favors a healthy glucose balance.

U.S. Pat. No. 5,759,539 in the name of David R. Whitmire, issued Jun. 2, 1998 ("Whitmore") suggests that oxygen generating formulations such as catalase and hydrogen peroxide may be useful in combination with enzymes that oxidize ethanol to acetate to treat ethanol overdose and to reduce the amount of ethanol in a subject. Whitmore suggests that oxygen is administered directly with a carrier or that an oxygen generator is administered. In Whitmore the oxygen or oxygen generator is administered together with enzymes that oxidize ethanol to acetate, and these components are delivered to a site where enzymatic conversion of ethanol to acetate is desired. Possible sites include the mucosal membrane of the mouth, nasopharyngeal region, or rectum. This approach would not be useful for modifying the microbiome in the colon for several reasons. For example: first, Whitmore teaches to deliver oxygen and enzymes to sites that would not result in an increase in oxygen in the colon; second, administration to reduce excess ethanol would be for a short term, whereas administration to modify the microbiome in the colon typically occurs over several days or weeks or months in order to realize a therapeutic benefit, such as weight management.

This invention meets needs in the art by providing pharmaceutical preparations that may be administered to a subject and that act in the colon of the subject to increase the oxygen tension and/or redox potential and/or pH of the colon, thus changing the conditions in which the gut microbiome of the colon exists. A hypothesis of this invention is that these endogenous changes to the environment of the colon will in turn change the relative abundance of various bacteria present in the colon in a manner that mimics, at least partially, changes to the gut microbiome previously observed in RYGB. Based in part on this discovery, the inventor provides herein methods comprising administering to a subject at least one agent that increases oxygen tension and/or redox potential and/or pH in the colon of a subject. In some embodiments the at least one agent is administered by administering an effective amount of the at least one agent to the small intestine and/or large intestine of the subject. Also provided are methods of treating a subject. In some embodiments the methods comprise providing a subject having or at risk of developing at least one condition selected from a metabolic disease or disorder, metabolic syndrome, cardiovascular disease, and excess weight; and administering a pharmaceutical composition of the invention to the subject, to thereby treat the at least one condition selected from a metabolic disease or disorder, metabolic syndrome, cardiovascular disease, and excess weight in the subject. These and other features and aspects of the invention are disclosed more fully herein.

B. Definitions

As used herein, "subject" means any mammal. In some embodiments the subject is a human. In some embodiments the subject is a primate. In some embodiments the subject is a non-human mammal, such as a non-human primate. In some embodiments the subject is a farm animal or livestock. In some embodiments the subject is a pet or companion animal.

As used herein, an "active agent" is a chemical entity that acts to increase the oxygen tension and/or redox potential and/or pH of an aqueous solution that approximates the conditions of a mammalian small intestine or large intestine. Such an agent is variously referred to herein as an "active agent" and/or as an "agent that increases oxygen tension and/or redox potential and/or pH in the colon of the subject to thereby manage the weight of the subject."

As used herein, an "agent that increases oxygen tension and/or redox potential and/or pH in the colon of the subject to thereby manage the weight of the subject" is an agent that has at least one property selected from (1) increases the oxygen tension of a solution of phosphate buffered saline (PBS), (2) increases redox potential of PBS, and (3) increases pH of PBS.

Whether an agent increases the oxygen tension of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases oxygen tension by at least a predetermined cutoff, then the test agent is identified as an active agent. Oxygen concentration is then measured using a commercially available dissolved oxygen meter. In some embodiments a test agent is identified as an active agent if the test agent increases the oxygen tension by at least 0.01 mg/L. In some embodiments a test agent is identified as an active agent if the test agent increases the oxygen tension by at least 0.02 mg/L. In some embodiments a test agent is identified as an active agent if the test agent increases the oxygen tension by at least 0.05 mg/L. In some embodiments a test agent is identified as an active agent if the test agent increases the oxygen tension by at least 0.10 mg/L. In some embodiments a test agent is identified as an active agent if the test agent increases the oxygen tension by at least 0.20 mg/L. In a preferred embodiment, the active agent increases the oxygen tension by at least 0.10 mg/L.

Whether an agent increases the redox potential of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases redox potential by at least a predetermined cutoff, then the test agent is identified as an active agent. Redox potential is then measured using a commercially available redox meter. In some embodiments a test agent is identified as an active agent if the test agent increases the redox potential by at least 0.1 mV. In some embodiments a test agent is identified as an active agent if the test agent increases the redox potential by at least 0.5 mV. In some embodiments a test agent is identified as an active agent if the test agent increases the redox potential by at least 1.0 mV. In some embodiments a test agent is identified as an active agent if the test agent increases the redox potential by at least 5.0 mV. In some embodiments a test agent is identified as an active agent if the test agent increases the redox potential by at least 10.0 mV. In some embodiments a test agent is identified as an active agent if the test agent increases the redox potential by at least 20.0 mV. In a preferred embodiment the active agent increases the redox potential by at least 10.0 mV.

Whether an agent increases the pH of PBS is measured in the following assay. A solution of phosphate buffered saline is provided. The PBS is 0.01 M phosphate buffered saline (NaCl 0.138 M; KCl—0.0027 M); pH 7.4, at 25° C. The test agent is added to the PBS in different concentrations ranging from 1 nano molar to 1 molar. The solution is then incubated at 37 C, and stirred at 20 rpm. Across titration within this concentration range, if the test agent increases redox potential by at least a predetermined cutoff, then the test agent is identified as an active agent. The pH of the solution is then measured using a commercially available pH meter. In some embodiments a test agent is identified as an active agent if the test agent increases the pH by at least 0.01 units. In some embodiments a test agent is identified as an active agent if the test agent increases the pH by at least 0.02 units. In some embodiments a test agent is identified as an active agent if the test agent increases the pH by at least 0.05 units. In some embodiments a test agent is identified as an active agent if the test agent increases the pH by at least 0.10 units. In some embodiments a test agent is identified as an active agent if the test agent increases the pH by at least 0.20 units. In a preferred embodiment the active agent increases the pH by at least 0.10 units.

A skilled artisan will appreciate that a single agent may have any two of these three activities or may have all three. That is, that a single agent may increase oxygen tension and also increase redox potential; or that a single agent may increase oxygen tension and also increase pH; or that a single agent may increase redox potential and also increase pH; or that a single agent may increase oxygen tension, and increase redox potential, and increase pH. Thus, in some instances an agent that is identified herein as an agent that increases one of oxygen tension, redox potential, and pH, that agent may also be an agent that increases at least one additional feature selected from oxygen tension, redox potential, and pH. A non-limiting example is sodium percarbonate, which increases all of oxygen tension, redox potential and pH.

While exemplary active agents are disclosed herein the disclosed agents are not intended to be limiting.

As used herein "condition" encompasses a disease, condition, or disorder.

The term "effective amount" refers to the amount of active agent that elicits a biological or medicinal response in a subject, including in a tissue or system of the subject, and that is being sought by a researcher, veterinarian, medical doctor, nutritionist, or other clinician or caregiver or by a subject, which includes one or more of the following:

(1) Preventing the condition, for example, preventing a condition in a subject that may be predisposed to the condition but does not yet experience or display the pathology or symptomatology of the condition;

(2) Inhibiting the condition, for example, inhibiting a condition in an individual that is experiencing or displaying the pathology or symptomatology of the condition (i.e., arresting further development of the pathology and/or symptomatology); and (3) Ameliorating the condition, for example, ameliorating a condition in an individual that is experiencing or displaying the pathology or symptomatology of the condition, (i.e., reversing the pathology and/or symptomatology).

As used herein, an "increase in the relative abundance" of a group of bacteria in the gut microbiota of a subject means an increase in the proportion of bacterial cells belonging to that group among the total bacterial cells measured in an assay that samples the bacteria in the microbiota of the gut of a subject. Relative abundance is defined as the number of bacteria belonging to that group divided by the total number of bacteria measured. For example, if 20% of taxonomic markers in the gut microbiota of a subject obtained by 16S rRNA sequencing belong to a given group of bacteria, the relative abundance of this group of bacteria is scored as 20%. In other words, there would be 20 bacteria belonging to this group in every 100 bacteria measured by sequencing or another equivalent method. Maximum relative abundance is 100% and the minimum is 0%.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. As used herein, "overweight" is defined as a BMI in the range 25-30 $kg/m^2$, and "obesity" or "obese" as a BMI greater than 30 $kg/m^2$.

As used herein the term "metabolic disorder", refers to disorders, diseases, and conditions that are caused or characterized by abnormal weight gain, energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 or other neurotransmitters or regulatory proteins in the brain) or the like. Some non-limiting examples can be obesity, diabetes, including type II diabetes, insulin-deficiency, insulin-resistance, insulin-resistance related disorders, glucose intolerance, syndrome X, inflammatory and immune disorders, osteoarthritis, dyslipidemia, metabolic syndrome, non-alcoholic fatty liver, abnormal lipid metabolism, cancer, neurodegenerative disorders, sleep apnea, hypertension, high cholesterol, atherogenic dyslipidemia, hyperlipidemic conditions such as atherosclerosis, hypercholesterolemia, and other coronary artery diseases in mammals, and other disorders of metabolism. In some embodiments the metabolic disorder is diagnosed by a physician.

As used herein the term "treat," "treating" or "treatment" refers to the administration of therapy to an individual who already manifests at least one symptom of a condition, or who has previously manifested at least one symptom of a condition, or who is identified as at risk of developing a condition. For example, "treating" can include alleviating, abating or ameliorating a condition's symptoms, preventing additional symptoms, ameliorating or preventing the underlying metabolic causes of symptoms, inhibiting the condition, e.g., arresting the development of the condition, relieving the condition, causing regression of the condition, relieving a second condition caused by the first condition, or stopping the symptoms of the condition either prophylacticly and/or therapeutically. For example, the term "treating" in reference to a condition includes a reduction in severity of one or more symptoms associated with a particular condition. Therefore, treating a condition does not necessarily mean a reduction in severity of all symptoms associated with a condition and does not necessarily mean a complete reduction in the severity of one or more symptoms associated with a condition. For example, a method for treatment of cardiovascular disease can result in a reduction in blood pressure; however, the reduction in blood pressure does not need to be enough such that the individual has a fully normal cardiovascular health. It has been shown that even modest decreases in weight or related parameters such as BMI, waist circumference and percent body fat, can result in improvement of health, for example, lower blood pressure, improved blood lipid profiles, or a reduction in sleep apnea. For example, the term "treating" also includes reducing the rate of increase in severity in a condition already manifested in a subject and/or reducing the rate of occurrence of new related conditions in the subject.

As used herein, "providing a subject having or at risk of developing at least one condition" refers to a judgment made by a researcher, veterinarian, medical doctor, nutritionist, or other clinician or caregiver, or by a subject, that a subject requires or will benefit or may benefit from treatment.

As used herein, "weight management" means at least one of weight loss, maintenance of weight, maintenance of weight loss (also called weight maintenance herein), controlling weight gain, body mass index (BMI) reduction, maintenance of BMI, maintenance of BMI reduction, and controlling BMI gain in a subject. In some embodiments the subject is overweight or obese. In some embodiments the subject has at least one weight-related condition. In some embodiments the at least one weight-related condition is selected from a metabolic disease or disorder, metabolic syndrome, and cardiovascular disease. In some embodiments the at least one weight-related condition is selected from hypertension, dyslipidemia, and type 2 diabetes. In some embodiments at least one symptom of the at least one weight-related condition is ameliorated. For example, weight management for an individual who is overweight or obese can mean losing weight with the goal of keeping weight in a healthier range. Also, for example, weight management for an individual who is overweight or obese can include losing body fat (reduction in BMI) or circumference around the waist with or without the loss of body weight. Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss. As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein. In some embodiments weight management comprises decreasing appetite. In some embodiments weight management comprises decreasing hunger.

As used herein, "aerobic bacteria" are bacteria that need oxygen to grow. Included within the aerobic bacteria are microaerophiles, which are bacteria that require oxygen for energy production but are harmed by atmospheric concentrations of oxygen.

As used herein, "facultative anaerobes" are bacteria or other microorganisms such as fungi that make ATP by aerobic respiration if oxygen is present, but are capable of switching to fermentation or anaerobic respiration if oxygen is absent.

As used herein, "sustained release" refers to a pharmaceutical formulation containing a composition comprising at least one active agent and at least one release rate modifier. The pharmaceutical formulation is formulated so that the at least one release rate modifier reduces the rate of release of the at least one active agent in comparison to a similar formulation that does not contain at least one release rate modifier. The pharmaceutical formulation may also be referred to as "formulated for sustained release" or as a "sustained release formulation." The pharmaceutical formulation may alternatively be referred to as "formulated for extended release" or as an "extended release formulation," making reference to the reduced rate of release that extends the period of release.

As used herein, "delayed release" refers to a pharmaceutical formulation containing a composition comprising at least one active agent and a composition coating that encases the at least one active agent and preventing its immediate release in the stomach following oral administration to a subject. The coating may be referred to as a "delayed release" coating. Generally the coating prevents the active agent from interacting chemically with components of the stomach such that the active agent is protected from the stomach environment and is only released from the coating once the microparticles reach the small intestine and/or colon. Examples of delayed release coatings are enteric coatings well known in the art. An alternative type of delayed release coating is a coating that is digested by bacterial enzymes present in the colon and absent from the stomach and/or the stomach and small intestine. Enteric coatings are well known in the art. In general, an enteric coating is a polymer barrier that prevents the dissolution or disintegration of an active agent in the gastric environment.

In some embodiments the period of release of active agent from a sustained release formulation is increased in comparison to a comparable formulation that does not comprise the at least one release rate modifier by a period of 0.5 hours, 1 hour, 2 hours, 3 hours, 4 hours, 5 hours, 6 hours, 12 hours, or 24 hours. In some embodiments the period of release of active agent from a sustained release formulation is increased in comparison to a comparable formulation that does not comprise the at least one release rate modifier by a period of at least 0.5 hours, at least 1 hour, at least 2 hours, at least 3 hours, at least 4 hours, at least 5 hours, at least 6 hours, at least 12 hours, or at least 24 hours.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination.

C. Agents That Increase Oxygen Tension and/or Redox Potential and/or pH

A skilled artisan will appreciate that any agent that increases oxygen tension and/or redox potential and/or pH (i.e., any active agent) may be used in the pharmaceutical preparations and methods of this invention.

Agents that increase oxygen tension include agents that carry oxygen to the large intestine and agents that increase production of oxygen from stores in the gut and/or from added oxygen stores. Any oxygen carrier may be used to increase oxygen tension, including a molecule that reacts to release oxygen. For example, in some embodiments the at least one agent comprises a peroxide functional group. A peroxide functional group is a group comprising or consisting of an O—O single bond or the peroxide anion. In contrast to oxide ions, the oxygen atoms in the peroxide ion have an oxidation state of −1. The simplest stable peroxide is hydrogen peroxide. In some embodiments at least one agent is hydrogen peroxide. In some embodiments the at least one peroxide is an organic peroxide. In some embodiments the at least one peroxide is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the at least one agent is an inorganic peroxide. In some embodiments the at least one agent is an inorganic peroxide selected from Ammonium persulfate, Calcium peroxide, Magnesium peroxide, Potassium persulfate, Sodium peroxide, Lithium peroxide, Barium peroxide and Sodium perborate. In some embodiments the at least one agent is carbamide peroxide. In some embodiments the at least one agent is Sodium percarbonate.

In some embodiments, sodium percarbonate is formulated as granules. In some embodiments sodium percarbonate granules are coated with protective coating or is chosen from commercially available coated particles such as FB 400C, FB 700C, OXYPER (Solvay), Provox-C (OCI corporation), ECOX-C (Kemira). The coating can be based on sodium carbonate, sodium chloride and sodium metasillicate or combinations thereof. Coating may be used to improve the stability of the final product.

In some embodiments, agents that increase oxygen tension are selected from reactive oxygen species (ROS) other than peroxides. Reactive oxygen species in the presence of catalysts or corresponding enzymes of mamalian or bacteria can be converted or decomposed into hydrogen peroxide or oxygen. In some embodiments one such agent is selected from superoxides, dioxygenyls, ozones and ozonides. In some embodiments one such agent is selected from singlet oxygen, hydroxyl radical, superoxide, nitric oxide, ozone, peroxyl, lipid peroxyl, hypochloric acid. In some embodiments, agents that increase oxygen tension are selected from reactive nitrogen species such as nitric oxide which can decompose into nitrogen and oxygen gas. In some embodiments, such agents are selected from nitrous oxide, peroxynitrite, peroxynitrous acid, nitrosoperoxycarbonate, dinitrogen trioxide, nitroxyl anion, nitrogen dioxide, nitrous acid, nitrousyl cation, nitryl chloride, nitrosonium cation, higher oxides of nitrogen, S-nitrosothiols, and dinitrosyl iron complexes.

In some embodiments, the agent that increases oxygen tension is an oxygen carrier. In some embodiments the oxygen carrier is a perfluorocarbon. In some embodiments the perfluorocarbon is selected from perfluorodecalin, bromoperfluoro-n-octane (perfluorobron), dichloroperfluoro-n-octane, triperfluoropropylamine. Oxygen gas may be dissolved in perfluorocarbon fluids and delivered to the colon with enteric coating or timed release technology. In some embodiments, the oxygen carrier is microbubble preparation of oxygen gas created by encapsulation of oxygen gas into polymetric bubbles or lipid based of emulsion of air/oxygen gas. In some embodiments, oxygen gas may be directly delivered to the gut to increase oxygen tension. In some embodiments, oxygen gas is encapsulated into enterically coated capsules and delivered to increase oxygen tension in the colon using pH or timed release formulations.

Agents that increase production of oxygen from stores in the gut and/or from added oxygen stores include any enzyme that catalyzes a chemical reaction that produces oxygen. An example is catalase, a common enzyme found in nearly all living organisms exposed to oxygen. Catalase catalyzes the decomposition of hydrogen peroxide to water and oxygen. Accordingly, in some embodiments the agent that increases oxygen tension is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In some embodiments the catalase is a plant catalase such as potato catalase. In some embodiments the catalase is liver catalase, such as bovine catalase. In some embodiments the catalase is blood catalase. In some embodiments the catalase is bacterial catalase. In some embodiments the catalase is obtained from *Microccocus* genus. In some embodiments the catalase is fungal catalase. In some embodiments the catalase is obtained from *Asperigillus niger*. In some embodiments the catalase is recombinant. In such embodiments catalase increases oxygen tension by increasing the rate of decomposition of endogenous hydrogen peroxide to water and oxygen. In other embodiments catalase and hydrogen peroxide are used together.

Additional examples of agents that catalyze a chemical reaction that produces oxygen include additional peroxide catalysts. In some embodiments the peroxide catalyst is an inorganic peroxide catalyst. In some embodiments the inorganic peroxide catalyst is selected from manganese(IV) oxide (manganese dioxide, $MnO_2$), lead(IV) oxide (lead dioxide, $PbO_2$), iron(III) oxide (red iron oxide, $Fe_2O_3$), silver nitrate and potassium iodide. In some embodiments the peroxide catalyst is an organic peroxide catalyst. In some embodiments the organic peroxide catalyst is selected from blood and bacteria. In some embodiments the organic peroxide catalyst is a peroxidase. Peroxidases are a large family of enzymes that typically catalyze a reaction of the form: ROOR'+electron donor (2 e−)+2H+→ROH+R'OH In some embodiments the at least one agent is an agent that increases pH. Non-limiting examples of agents that increase pH include bicarbonate salts, carbonate salts, bases, and buffers. In some embodiments the agent that increases pH is bicarbonate. Bicarbonate acts physiologically to regulate pH in the small intestine. It is released from the pancreas in response to the hormone secretin to neutralize the acidic chyme entering the duodenum from the stomach. In some embodiments the at least one agent is bicarbonate. In some embodiments the at least one agent comprises a bicarbonate group. Examples include bicarbonate salts, such as sodium bicarbonate, potassium bicarbonate, caesium bicarbonate, magnesium bicarbonate, calcium bicarbonate, ammonium bicarbonate. In some embodiments the at least one agent is a bicarbonate salt. In some embodiments the bicarbonate salt is selected from Sodium Hydrogen Carbonate, Beryllium Hydrogen Carbonate, Magnesium Hydrogen Carbonate, Calcium Hydrogen Carbonate, Potassium Hydrogen Carbonate, Barium Hydrogen Carbonate, Copper(II) Hydrogen Carbonate, Iron(III) Hydrogen Carbonate, Aluminum Hydrogen Carbonate, Lithium Hydrogen Carbonate, Lead (II) Hydrogen Carbonate, Tin(IV) Hydrogen Carbonate, Iron(II) Hydrogen Carbonate, Ammonium Hydrogen Carbonate, Mercury(II) Hydrogen Carbonate, Lead(IV) Hydrogen Carbonate, Manganese(II) Hydrogen Carbonate, Cesium Hydrogen Carbonate, Silver Hydrogen Carbonate, Tin Hydrogen Carbonate, Copper(I) Hydrogen Carbonate, Zinc Hydrogen Carbonate, Rubidium Hydrogen Carbonate, Nickel(II) Hydrogen Carbonate, Cadmium Hydrogen Carbonate, Strontium(II) Hydrogen Carbonate, Mercury(I) Hydrogen Carbonate, Chromium(II) Hydrogen Carbonate, Gold(III) Hydrogen Carbonate, Cobalt(II) Hydrogen Carbonate, and Cobalt(III) Hydrogen Carbonate.

In some embodiments the at least one agent is a carbonate. In some embodiments the carbonate is a carbonate salt. In some embodiments the carbonate salt is selected from Sodium Carbonate, Sodium percarbonate (Sodium Carbonate Peroxide), Calcium Carbonate, Cobalt(III) Carbonate, Copper(I) Carbonate, Potassium Carbonate, Ammonium Carbonate, Chromium(III) Carbonate, Iron(III) Carbonate, Aluminum Carbonate, Tin(IV) Carbonate, Lead(IV) Carbonate, Magnesium Carbonate, Iron(II) Carbonate, Tin(II) Carbonate, Chromium(VI) Carbonate, Silver(I) Carbonate, Titanium(IV) Carbonate, Vanadium(III) Carbonate, Copper (II) Carbonate, Zinc(II) Carbonate, Lithium Carbonate (Lithium Salt), Cobalt(II) Carbonate, Nickel(III) Carbonate, Sodium Carbonate Decahydrate, Mercury(I) Carbonate, Barium Carbonate, Lead Carbonate, Mercury(II) Carbonate, Chromium(II) Carbonate, Strontium Carbonate, and Vanadium(V) Carbonate.

In some embodiments the at least one agent is a base. In some embodiments the base is a strong base, such as a base selected from Sodium Hydroxide, Aluminum Hydroxide, Calcium Hydroxide, Barium Hydroxide, Magnesium Hydroxide, Iron(III) Hydroxide, Ammonium Hydroxide, Potassium Hydroxide, Chromium(III) Hydroxide, Zinc Hydroxide, Lead(II) Hydroxide, Platinum(IV) Hydroxide, Vanadium(V) Hydroxide, Beryllium Hydroxide, Copper(II) Hydroxide, Lead(IV) Hydroxide, Vanadium(III) Hydroxide, Iron(II) Hydroxide, Nickel(II) Hydroxide, Tin(IV) Hydroxide, Silver Hydroxide, Strontium Hydroxide, Tin(II) Hydroxide, Lithium Hydroxide, Manganese(II) Hydroxide, Chromium(II) Hydroxide, Nickel Oxo-hydroxide, Mercury (II) Hydroxide, Cadmium Hydroxide, and Copper(I) Hydroxide, Manganese(IV) Hydroxide. In some embodiments the base is a superbase, such as a base selected from Butyl lithium (n-C4H9Li), Lithium diisopropylamide (LDA) [(CH3)2CH]2Nli, Lithium diethylamide (LDEA) (C2H5)2Nli, Sodium amide (NaNH2), Sodium hydride (NaH), and Lithium bis(trimethylsilyl)amide [(CH3) 3Si2NLi. In some embodiments the base is an organic base, such as a base selected from Amines, Nitrogen-containing heterocyclic compounds, Urea, Ammonia, pyridine, methyl amine, imidazole, benzimidazole, histidine, and phosphazene. In some embodiments the agent is a weak base.

In some embodiments the agent is a buffer, such as a buffer selected from MES, Bis-Tris, ADA, aces, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, and CABS. In some embodiments the buffer is a Citric Acid—Na2HPO4 Buffer Solution. In some embodiments the buffer is a Na2HPO4-NaH2PO4 Buffer Solution. In some embodiments the buffer is a Sodium Carbonate-Sodium Bicarbonate Buffer Solution. In some embodiments the buffer is a Imidazole (glyoxaline) —HCl buffer solution.

In some embodiments the at least one agent is an agent that increases redox potential. In some embodiments, the agent that increases redox potential is an oxidizing agent. In some embodiments, the oxidizing agent is selected from compounds containing halogens such as Fluorine (F), Chlorine (Cl), Bromine (Br), Iodine (I), and Astatine (At). In some embodiments, the oxidizing agent is selected from Aluminium nitrate, Ammonium chlorate, Ammonium dichromate, Ammonium nitrate, Ammonium nitrite, Ammonium perchlorate, Ammonium permanganate, Ammonium persulfate, Antimony pentachloride, Barium chlorate, Barium chromate, Barium manganate, Barium nitrate, Barium perchlorate, Barium peroxide, Benedict's reagent, Bismuth pentafluoride, Bromic acid, Bromine, Bromine monochloride, Bromine pentafluoride, Bromine trifluoride, Bromous acid, Cadmium nitrate, Caesium chromate, Caesium nitrate, Caesium perchlorate, Calcium bromate, Calcium chlorate, Calcium chromate, Calcium hypochlorite, Calcium iodate, Calcium nitrate, Calcium permanganate, Calcium peroxide, Ceric ammonium nitrate, Cerium(III) methanesulfonate, Chloric acid, Chlorine, Chlorine monofluoride, Chlorine nitrate, Chlorine pentafluoride, Chlorine trifluoride, Meta-Chloroperoxybenzoic acid, N-Chlorosuccinimide, Chlorous acid, Chromate and dichromate, Chromic acid, Chromium nitrate, Chromyl chloride, Chromyl fluoride, Cobalt(II) chlorate, Cobalt(II) nitrate, Collins reagent, Copper(II) acetate, Copper(II) hydroxide, Copper (II) nitrate, Copper(II) perchlorate, Dess-Martin periodinane, Dichlorine heptoxide, Dinitrogen tetroxide, Dioxygen difluoride, Fehling's solution, Fenton's reagent, Fluorine, Fluorine perchlorate, Gadolinium(III) nitrate, Hill reagent, Hydrazine nitrate, Hydrogen peroxide, Hydrogen peroxideurea, Hypobromous acid, Hypochlorous acid, Hypoiodous acid, Iodic acid, Iodine, Iodine heptafluoride, Iodine monochloride, Iodine pentafluoride, Iodine pentoxide, Iodine trichloride, Iodobenzene dichloride Iodous acid, Iron(III) chromate, Iron(III) nitrate, Jones reagent, Lead(II) chromate, Lead(II) nitrate, Lead(IV) acetate, Lithium chlorate, Lithium hypochlorite, Lithium nitrate, Lithium nitrite, Lithium perchlorate, Lithium peroxide, Magnesium monoperoxyphthalate, Magnesium nitrate, Magnesium perchlorate, Manganese(III) acetate, Mercury(II) nitrate, Nickel chromate, Nickel(II) nitrate, Nitronium perchlorate, Nitrosyl-Ohydroxide, Nitrous acid, Osmium tetroxide, Oxygen, Oxygen difluoride, Ozone, Palladium(II) nitrate, Perbromic acid, Perchlorate, Perchloric acid, Performic acid, Periodic acid, Permanganic acid, Peroxy acid, Peroxymonosulfuric acid, Potassium bromate, Potassium chromate, Potassium dichromate, Potassium hypochlorite, Potassium iodate, Potassium nitrate, Potassium nitrite, Potassium perchlorate, Potassium periodate, Potassium permanganate, Potassium peroxide, Potassium peroxymonosulfate, Potassium persulfate, Potassium superoxide, Potassium tetraperoxochromate(V), Potassium trioxochlorochromate, Pyridinium chlorochromate, Rubidium nitrate, Rubidium perchlorate, Scandium nitrate, Selenic acid Selenium hexasulfide, Selenium trioxide, Selenous acid, Silver bromate, Silver chlorate, Silver chromate, Silver dichromate, Silver iodate, Silver nitrate, Silver perchlorate, Singlet oxygen, Sodium bromate, Sodium chlorate, Sodium chlorite, Sodium chromate, Sodium dichromate, Sodium hypochlorite, Sodium fluoride, Sodium iodate, Sodium nitrate, Sodium nitrite, Sodium perborate, Sodium percarbonate, Sodium perchlorate, Sodium periodate, Sodium permanganate, Sodium peroxide, Sodium persulfate, Sodium superoxide, Stannous fluoride, Strontium bromate, Strontium chloride, Strontium nitrate, Strontium peroxide, Sulfuric acid, Superoxidant, Telluric acid, Tetrapropylammonium perruthenate, Thallium(III) nitrate, Tollens' reagent, Trinitroethylorthocarbonate, Trinitroethylorthoformate, Uranyl nitrate, Uranyl peroxide, Zinc chlorate, Zinc nitrate, and Zinc peroxide. In some embodiments, the agent that increases redox potential is a fluoride containing compound. In some embodiments, the agent that increases redox potential is selected from Sodium fluoride, Sodium monofluorophosphate and Stennous fluoride.

D. Pharmaceutical Preparations

This invention provides pharmaceutical preparations comprising a plurality of particles, each particle comprising: 1) a core comprising at least one agent that increases oxygen tension and/or redox potential and/or pH in the colon of a subject following administration to the subject, and 2) an enteric coating encasing the core.

This invention also provides pharmaceutical preparations comprising a plurality of particles and a capsule or sachet encasing the plurality of particles. In some embodiments the pharmaceutical preparation comprises: A) A plurality of particles, each particle comprising: 1) a core comprising at least one agent that increases oxygen tension and/or redox potential and/or pH in the colon of a subject following administration to the subject, and 2) an enteric coating encasing the core; and B) a capsule or sachet encasing the plurality of particles.

The pharmaceutical preparations of the invention typically comprise a plurality of particles, each particle comprising: 1) a core comprising at least one agent that increases oxygen tension and/or redox potential and/or pH in the colon of a subject following administration to the subject, and 2) an enteric coating encasing the core. In some embodiments the cores of the plurality of particles have maximum dimensions of from 0.1 to 2 mm. In some embodiments the cores of the plurality of particles have maximum dimensions of from 0.2 to 1.0 mm. In some embodiments the cores of the plurality of particles have maximum dimensions of from 0.4 to 1.2 mm. In some embodiments the cores of the plurality of particles have maximum dimensions of from 0.6 to 1.4 mm. In some embodiments the cores of the plurality of particles have maximum dimensions of from 0.8 to 1.6 mm. In some embodiments the cores of the plurality of particles have maximum dimensions of from 1.0 to 1.8 mm. In some embodiments the cores of the plurality of particles have maximum dimensions of from 0.4 to 0.8 mm. In some embodiments the plurality of particles have maximum dimension of no more than 3.0 mm. In some embodiments the plurality of particles have maximum dimension of no more than 2.5 mm. In some embodiments the plurality of particles have maximum dimension of no more than 2.0 mm. In some embodiments the plurality of particles have maximum dimension of no more than 1.5 mm. In some embodiments the plurality of particles have maximum dimension of no more than 1 mm. In some embodiments the plurality of particles have maximum dimensions of from 2.0 to 3.0 mm. In some embodiments the plurality of particles have maximum dimensions of from 1.5 to 2.5 mm. In some embodiments the plurality of particles have maximum dimensions of from 1.0 to 2.0 mm. In some embodiments the plurality of particles have maximum dimensions of from 2.5 to 3.0 mm. In some embodiments the plurality of particles have maximum dimensions of from 2.0 to 2.5 mm. In some embodiments the plurality of particles have maximum dimensions of from 1.5 to 2.0 mm. In some embodiments the plurality of particles have maximum dimensions of from 1.0 to 1.5 mm.

In some embodiments the core consists of the active agent. In some embodiments the core consists of a plurality of active agents. In some embodiments the core comprises at least one active agent. In some embodiments the core comprises at least one active agent and at least one release rate modifier. In some embodiments the core consists of at lease one active agent and the core is coated by a release rate modifier.

The release rate modifier controls the rate of release of the at least one active agent when the in the small intestine. In some embodiments, the release rate modifier is a polymer that is degraded by the gut microbiota selected from azopolymers, starches, dextrans, mucopolysaccharides (e.g. inulin, guar gum, pectin, chondroitin sulfate, alginic acid). In some embodiments the release rate modifier comprises a hydrophobic material, such as a waxy solid. Exemplary waxes suitable to use as the hydrophobic material include hydrocarbon waxes, such as paraffin wax and the like, which are substantially or entirely free of unsaturation. Exemplary paraffin waxes are higher alkanes and mixtures of higher alkanes of the general formula $C_nH2_{2n+2}$, where typically, $20<n<50$, and thus have no unsaturation. They are solid at ambient temperatures and melt-processable.

In some embodiments the release rate modifier comprises a hydrophilic material. In some embodiments the hydrophilic material is a hydrophilic organic polymer which is capable of hydrogen bonding and solid at ambient temperatures (25° C.), hydrophilic and/or water soluble powders, and combinations thereof. In some embodiments the release rate modifier comprises a hydrophilic material and a hydrophobic material. That is, it comprises a plurality of materials and and least one of the materials is more hydrophilic than at least a second material (that is in turn more hydrophobic than the first material).

In some embodiments the hydrophilic material is dispersed in the hydrophobic material. In the case of organic polymers, the hydrophilic material may be a material which is insoluble or substantially insoluble in the hydrophobic material such that it forms discrete regions where it is of high concentration in the hydrophobic material (or forms a separate). The regions may be spaced from each other by the hydrophobic material. In the case of hydrophilic and/or water soluble powders, the powder may be dispersed throughout the hydrophobic material, or in one embodiment, more highly concentrated near an outer surface thereof.

In the case of hydrophilic and/or water soluble powders as release rate modifiers, these may be present in a total concentration of from 0.001 wt. % to 30 wt. %, such as 0.1-20 wt. %, or 1.0 to 10 wt. %. Examples of hydrophilic powders include anhydrous inorganic particles, such as silicon dioxide, e.g., hydrophilic silica and silica nanopowders. Exemplary water-soluble powders include water-soluble acids and salts thereof, such as anhydrous phosphate salts, e.g., sodium polyphosphate, sodium tripolyphosphate, sodium pyrophosphate; anhydrous citric acid and salts thereof, such as alkali metals salts, e.g., sodium citrate; anhydrous sodium sulfate, anhydrous magnesium salts, such as magnesium sulfate and magnesium chloride. Combinations of such release agents may be employed. The hydrophilic and/or water soluble powders, such as silica, may have an average particle size of, for example, 1-100 nanometers (nm), e.g., 5-20 nm, and a surface area of, for example 50-400 $m^2/g$. Hydrophilic fumed silica, for example, may be obtained under the tradename AEROSIL™ from Evonik Industries with a specific surface area (measured by the BET method) in the range of 90-300 $m^2/g$. As an example, AEROSIL™ 200 has a specific surface area of 200 $m^2/g$.

When hydrophilic organic polymers are used as release rate modifiers, these may be present at a total concentration of from 0.5 wt. % to 40 wt. %, e.g., 1-35 wt. %, or 10-30 wt. %. In one embodiment, the hydrophilic polymer has a melting point of at least 30° C. or at least 40° C., such as up to 80° C. The hydrophilic polymer can have a weight average molecular weight of at least 300. Examples of suitable hydrophilic organic polymers include polyalkylene glycols, such as polyethylene glycol and polypropylene glycol, and esters thereof, polyamide compounds (e.g., polyvinylpyrrolidone), poly(vinyl acetate), poly(vinyl alcohol), poly(acrylic acid), polyacrylamide, polyoxylglycerides, such as lauroyl, oleoyl, and stearoyl polyoxylglycerides, which are mixtures of monoesters, diesters, and triesiers of glycerol and monoesters and diesters of polyethylene glycols (e.g., lauroyl macrogolglycerides, such as GELUCIRE™ 44/14, available from Gattefosse, which has a melting point of 44° C. and an HLB of 14), and ethylene oxide derivatives thereof, poloxamers, which are triblock copolymers having a central hydrophobic block of poly(propylene oxide) and two side blocks of poly(ethylene oxide) (e.g., poloxamer 188, which has a melting point 52° C.), and derivatives thereof, and mixtures thereof.

Exemplary polyethylene glycols (PEG) suitable for the release rate modifier may have a weight average molecular weight of from 300 daltons to 50,000 daltons, such as about 600-35000, or 1000 to 5,000 daltons. Such materials are commercially available as PEG 1000 (melting point 37-40° C.), PEG 1500 (melting point 44-48° C.), PEG 2000 (melting point 49-52° C.), and the like. A combination of polyethylene glycols having different molecular weights may be employed to tailor the release rate. For example a mixture may be formed by combining, e.g., in a ratio of from 1:10 to 10:1, a polyethylene glycol having a molecular weight of about 500-1200 (on average), such as PEG 1000, with a polyethylene glycol having a molecular weight of at least 1500 or at least 1800 (on average), such as PEG 1500 or PEG 2000. In one embodiment, a combination of PEGs with average molecular weight ranging from 300 daltons to 50,000 daltons may be mixed on appropriate amounts to provide a mixture which is liquid at a temperature of 35-70° C., such as 45-60° C. For example, PEG with an average molecular weight of 20,000 and PEG 1500 have melting points of 60-65° C. and 44-48° C., respectively, and a mixture of PEG 1500 and PEG 20,000 may be liquid at about 55° C., depending on the ratio.

In the case of hydrophilic organic polymers, such as PEG, discrete regions in which the polymer is localized may have an average size of, for example, at least 0.1 or at least 0.5 nm, and can be up to 100 nm, or up to 20 nm, e.g., 0.5-5 nm. For example, the hydrodynamic radius of glycerol is 0.3 nm and that of PEG 1000, PEG 2000 and PEG 4000 is approximately 0.9, 1.4 and 1.9 nm, respectively.

A ratio of hydrophobic material to the hydrophilic material in the release rate modifier may be from 1:99 to 99:1, expressed by weight, such as from 2:98 to 98:2, or from 10:90 to 90:10, or from 15:85 to 85:15. The ratio can be at least 30:70, or at least 40:60, or at least 60:40. For example, in the case of polymers, such as PEG, the ratio of hydrophobic material to release rate modifier may be about 60:40 or about 50:50. For hydrophilic and/or water soluble powders, the ratio of hydrophobic material to the release rate modifier may be higher, such as at least 85:15, or at least 90:10.

In some embodiments, the hydrophilic material increases the rate of release of the active ingredient, as compared with the hydrophobic material alone. For example, the amount of active ingredient released (e.g., expressed as weight of hydrogen peroxide), may be at least 10% greater or at least 50% greater, over an initial period of two hours, than for the equivalent dosage form formed without the hydrophilic material, when exposed to the same aqueous conditions (e.g., a buffered release medium, at a temperature of 30-40° C.).

In some embodiments, the release rate modifier may provide a more uniform rate of release of the active agent than equivalent dosage forms formed without the release rate modifier, when exposed to the same aqueous conditions (e.g., buffered release medium at a temperature of 30-40° C.). For example, the initial release rate (expressed as wt. of active agent/hr), over about two hours, may be, on average, less than that of an equivalent dosage form without the release rate modifier and may be, on average, higher than that of equivalent dosage form in the subsequent two hour period.

In some embodiments, the exemplary dosage form formed with the release rate modifier release at least 10%, or at least 20%, or at least 30%, or at least 40%, or at least 50%, or at least 60%, or at least 70%, or at least 80%, or at least 90% by weight of the total amount of active agent that they contain over a period of 4 hours, 6 hours, or 8 hours after contact with the small intestine or aqueous medium at 30°-40° C. In some embodiments, the exemplary dosage form formed with the release rate modifier release less than 25% or less than 50% by weight of the total amount of active agent that they contain over a period of 2 hours after contact with the small intestine or aqueous medium at 30°-40° C.

As will be appreciated from the foregoing, the amount and type of release rate modifier can be selected to tailor the release rate according to the desired application.

In some embodiments, the release rate modifier further includes an emulsifier, dispersed in the hydrophobic material. Exemplary nonionic surfactants suitable as emulsifiers include fatty acids, polyol fatty acid esters, such as polyglyceroi esters, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), sugar esters, sorbitan esters, polysorbates, amine oxides and combinations thereof. As examples of suitable emulsifiers, nonionic surfactants with a low hydrophile-lipophile balance (HLB) may be used. The HLB may be from 2-5. Surfactants that are able to form micelles are able to improve the stability of hydrogen peroxide. Examples of these emulsifiers include C12-C24 fatty acids, such as lauric acid (CI 2), myristic acid (C14), palmitic acid (C16), stearic acid (C18), oleic acid (C18), linoleic acid (CI 8), and mixtures thereof. Such fatty acid emulsifiers can be obtained from Sigma-Aldrich under the tradename SPAN™, such as SPAN™ 60, which has an HLB of 4.7, SPAN™ 65, with an HLB of 2.1, SPAN™ 80, with an HLB of 4.3. Exemplary polyglycerol esters include polyglycerol polyricinoleate (PGPR), which has an HLB of 3, and is available from Evronik Industries, Essen Germany, or Danisco. A blend of surfactants having a high HLB and low HLB value may be used.

In some embodiments the pharmaceutical preparation comprises from 10 to 1000 particles, from 10 to 100, from 100 to 200, from 200 to 300, from 300 to 400, from 400 to 500, from 500 to 600, from 600 to 700, from 700 to 800, from 800 to 900, or from 900 to 1000 particles. In some embodiments the pharmaceutical preparation comprises from 50 to 100, from 50 to 200 or from 100 to 500 particles.

A delayed release coating is applied to the core to form particles in order to delay the release of active ingredients until the particle has passed through the acidic environment of the stomach and has reached the small intestine and/or colon. The physical chemical environment of the stomach and gastric physiology are highly variable, subject to multiple factors such as disease state, medication, age, and eating. For example in the fasted state stomach, the pH is less than 2 in healthy individuals, and gastric emptying occurs approximately every 30 minutes. However in the fed state (immediately after a meal), gastric emptying is delayed for 2 to 4 hours and gastric pH can be as high as pH 4.

For these reasons, in some embodiments the delayed release coating system is flexible. In some embodiments the pharmaceutical preparation is recommended to be taken on an empty stomach. In that case the delayed release coating may be resistant to the acidic stomach environment for a relatively short time and would not be expected to be subjected to strong mechanical attrition in the stomach. On the other hand, to allow for possible ingestion in the fed state, or where subsequent release from the intestine is not intended to be immediate, the coating may typically be sufficiently robust to withstand prolonged attrition in the stomach or to generally release more slowly in the alkaline environment.

The delayed release coating is typically (but not always) an enteric coating. There is a long history of use of enteric coatings on tablets and smaller multi-particulate dosage forms in the pharmaceutical industry. Generally polymers with acidic functional groups are chosen for enteric coatings. In the acid environment of the stomach these acid groups of the polymers are un-ionized, thus rendering the polymer water insoluble. However in the more neutral and alkaline pH of the intestine (pH 6.8-7.2), the functional groups ionize and the polymer film coating becomes water soluble.

Examples of enteric film coatings that may be used in embodiments of the invention include methacrylic acid copolymers, polyvinyl acetate phthalate, cellulose acetate phtallate, hydroxypropyl methylcellulose phthalate and hydroxypropyl methylcellulose acetylsuccinate. In some embodiments these water soluble coatings are applied from organic solvent based coating solutions. In some embodiments an aqueous based dispersion and/or pseudo-latex system of comprising at least one of the above polymers is used. In some embodiments the polymers used for enteric coating are found in the Food Chemicals Codex (FCC), have direct food additive status, and/or have generally regarded as safe (GRAS) status. In some embodiments, commercially available enteric coatings such as EUDAGRIT™ coatings (Evonik Industries) are used. In some embodiments, EUDAGRIT™ enteric coatings for dissolution at specific pH levels such as pH above 5.5 (Eudragit® L30D-55), pH above 5.6, pH above 6.0, pH above 6.8 (Eudragit®FS 30D) and pH above 7.0 (Eudragit®S100) are used. In some embodiments, the core of the formulation includes solid powder of an anionic copolymer matrix based on methacrylic acic and methyl methacrylate such as Eudagrit S 100 in order to achieve pH dependent sustained release of actives in distal ileum and colon. EUDRAGIT® FS 30 D is the aqueous dispersion of an anionic copolymer based on methyl acrylate, methyl methacrylate and methacrylic acid. The ratio of the free carboxyl groups to the ester groups is approx. 1:10.

Several strategies may be used to provide a food grade enteric coating for the pharmaceutical preparations of the invention. For example, an aqueous ethylcellulose (EC) based pseudo-latex may be used in conjunction with sodium alginate. For example, in some embodiments the Nutrateric™ nutritional enteric coating system marketed by Colorcon Inc. of Westpoint, Pa. is used. This coating is supplied as a two component system in the form of an aqueous ammoniated EC dispersion with 25% solids and a separate container of sodium alginate in powder form. To prepare the final coating solution, the sodium alginate is first dispersed and dissolved in water for 60 minutes and EC dispersion is then added to the alginate solution, ensuring that the amount of water used is appropriate to achieve a final recommended dispersed solids concentration of 10% by weight.

An alternative approach is the use of shellac on its own or in combination with other additives. Shellac is a natural, food approved, resinous material obtained from the exudate of the insect *Karria lacca*. It is a complex mixture of materials. The two main components with enteric properties being shelloic and aleuritic acid. Shellac may be used in the form of organic solvent based solutions. To obviate the use of solvents, neutralized aqueous shellac solutions are commercially available. EP 1 579 771 A1 describes a water based shellac dispersion which comprises shellac, a basic amino acid, a basic phosphate and water. The basic amino acid being selected from the group consisting of arginine, lysine and ornithine. Several forms of aqueous ammoniated shellac dispersions are also commercially available, for example Certiseal® FC 300A film coat product, manufactured by Mantrose Haeuser, a subsidiary of RPM Corporation. Esterification of the shellac is also limited in these systems as shellac forms a salt with the ammonia or protonated amino acid.

In another approach an enteric coating formulation in the form of a spray solution or suspension is used. This system may comprise shellac in aqueous salt form and sodium alginate, preferably in equal concentrations. An aqueous solution of an alkali salt of shellac is prepared by first dissolving the shellac in 55° C. hot water, then adding 10% ammonium hydrogen carbonate and heating to 60° C. and stirring for 30 minutes. Separately, a sodium alginate solution is prepared and the two solutions are then blended together. The system, when coated onto a dosage form rapidly disintegrates in simulated intestinal fluid (pH 6.8).

The above approaches describe enteric coatings composed of food approved ingredients, which are either pH sensitive or more time dependent in terms of their delayed release mechanism. However, all these systems require multiple, time consuming preparation steps, often requiring two separate solutions to be made with additional dilution requirements and which increases the potential for error. Alternately, the systems require the use of pre-made dispersions of EC or shellac, which then require further dilution and blending steps thereby adding cost, complexity and/or time to the manufacturing process.

In the case of pre-made aqueous dispersions, a further cost is incurred due to the need to store and ship dispersions which contain the added bulk of water. Additionally, these pre-made aqueous dispersions require additional precautions to be taken to control microbial contamination and to minimize any physical and/or chemical instability of the dispersion.

In some embodiments a formulation in powder form useful for producing a sprayable dispersion for enteric coating is used. The powder formulation comprising a food grade shellac, a non-ammonium alkali salt, and optionally a water-miscible polymer. The powder formulation when dispersed in water is capable of producing a sprayable dispersion for enteric coating. This coating at 15% solids in water has a viscosity of below 500 cps at about 25° C. when measured with a Brookfield LTV viscometer with a #2 spindle at 100 rpm.

In some embodiments the enteric coating comprises food grade shellac, optionally blended with other food grade ingredients. The coating is produced starting from a powder form dispursed in water. In addition to shellac, the coating may comprise a non-ammonium alkali salt, which may be selected from sodium bicarbonate, sodium carbonate, potassium carbonate, potassium bicarbonate, calcium hydroxide, calcium bicarbonate and calcium carbonate, and optionally a water-miscible polymer. The water-miscible polymer may be a polymer which is "food grade", dissolvable or dispersible in water, with no discernable phase separation from the aqueous phase. The water-miscible polymers that may be used include alginate salt, alginic acid, proteins (e.g. wheat, soybean or corn), methylcellulose (MC), hydroxypropylcellulose (HPC), hydroxypropylmethylcellulose (HPMC), carboxymethyl cellulose (CMC), pectin, carrageenan, guar gum, locust bean gum, xanthan gum, gellan gum, arabic gum, etc. In some embodiments the water-miscible polymer is selected from anionic polymers such as sodium carboxymethyl cellulose (CMC), sodium alginate or pectin. The coating may optionally comprise one or more plasticizers chosen from glycerine, mineral oil, triacetin, polyethylene glycol, glyceryl monostearate, acetylated monoglyceride, glyceryl tricaprylate/caprate and polysorbate. Optionally, the coating may further comprise pigments, and/or detackifiers such as titanium dioxide, talc, iron oxide glyceryl monostearate. Additional components such as natural colors, various carbohydrate derivatives such as hypromellose, hydroxypropyl cellulose, carboxymethyl starch, carageenan and xanthan may also be present.

The non-ammonium alkali salt used in the enteric coating composition may be any food grade, nonvolatile, water soluble inorganic or organic salt species. The non-ammonium alkali salt may be selected from sodium, potassium, calcium, magnesium, aluminum salts. In some embodiments the non-ammonium alkali salt comprises sodium bicarbonate. The amount of non-ammonium alkali salt of use in the enteric coating of is typically in the range of from 1.5% to 15% by weight of the coating, such as from 1.5% to 8% by weight of the coating.

If the coating comprises a plasticizer, the plasticizer may be selected from glycerine, propylene glycol, mineral oil, triacetin, polyethylene glycol, acetylated monoglyceride, glyceryl monostearate, glyceryl tricaprylate/caprate, polysorbate andoleic acid. Various edible oils may also serve as the plasticizers. The plasticizer may also be a medium-chain triglyceride which is a medium-chain (6 to 12 carbons) fatty acid ester of glycerol. If glycerine is the plasticizer, then it may be used in an amount in the range of from about 1% to about 10% by weight, such as from 2% to 6% by weight. If mineral oil is the plasticizer, then it may be used in an amount in the range of from 3% to 9%, such as from 5% to 7% by weight. If glyceryl monostearate is the plasticizer, then it may be used in an amount in the range of from 3% to 25%, such as about 5% to about 20% by weight. If polysorbate 80 is the plasticizer, then it may be used in an amount in the range of from 0.5% to 12%, such as from 2% to 10% by weight. If acetylated monoglyceride is the plasticizer, then it may be used in an amount in the range of from 2% to 12%, such as from 4% to 10% by weight.

In some embodiments the enteric coating protects the active agent until it reaches the distal ileum so that the active agent is then released in the distal ileum or the distal ileum and the large intestine, resulting in addition of oxygen to the large intestine in an amount sufficient to modify the microbiome of the large intestine. In some embodiments the enteric coating protects the active agent until it reaches the large intestine so that the active agent is then released in the large intestine, resulting in addition of oxygen to the large intestine in an amount sufficient to modify the microbiome of the large intestine. In some embodiments the enteric coating protects the active agent until it reaches the distal ileum and/or large intestine and so that it is then released over a period of at lease three hours, at least six hours, or at least twelve hours to thereby modify the microbiome of the large intestine for a period of time.

In some embodiments of the particles, the weight ratio of delayed release coating to core is from 5% to 50%. In some embodiments of the particles the weight ratio of delayed release coating to core is from 20% to 30%. In some embodiments of the particles the weight ratio of delayed release coating to core is from 30% to 40%. In some embodiments of the particles the weight ratio of delayed release coating to core is from 40% to 50%.

In some embodiments the delayed release coating prevents release until the active agent reaches the small intestine. In some embodiments the delayed release coating prevents release until the active agent reaches the ileum. In some embodiments the delayed release coating prevents release until the active agent reaches the distal ileum. In some embodiments the delayed release coating prevents release until the active agent reaches the colon.

In some embodiments the delayed release coating is an enteric coating that is protective at pH below 5.5. In some embodiments the enteric coating is protective at pH below 6.5. In some embodiments the enteric coating is protective at pH below 7.0. In some embodiments the enteric is protective at pH below 7.4. In some embodiments the delayed release coating is Eudagrit FS30D.

In some embodiments the particles comprise a core, a delayed release coating encapsulating the core, and a subcoat layer that encases the core and is disposed between the core and the delayed release coating. The subcoat layer may serve to protect the core during manufacturing and in particular application of the delayed release coating. Alternatively, or in addition, the subcoat layer may serve as a release rate modifier. Thus, the subcoat layer may be chosen from any release rate modifier known in the art, including any release rate modifier disclosed herein. In alternative embodiments the subcoat layer does not have release rate modification properties. Nonlimiting examples of subcoat layers include HPMC and guar gum.

In some embodiments the particles further comprise a subcoat layer that encases the core and is disposed between the core and the enteric coating. In some embodiments the subcoat layer comprises HPMC.

In some embodiments the plurality of particles is encased in a capsule or sachet. The capsule or sachet is generally chosen to deliver the plurality of particles to the stomach. In most embodiments the capsule or sachet is of a type that immediately releases the contents into the stomach.

In some embodiments of the pharmaceutical preparations the plurality of particles is suspended in liquid for oral administration.

In some embodiments of the pharmaceutical preparations the plurality of particles is compressed with an excipient to form a tablet for oral administration.

In some embodiments of the pharmaceutical preparations the plurality of particles is encased in a capsule or suspended in liquid for rectal administration as a suppository.

In some embodiments the pharmaceutical preparation comprises no more than one active agent. In some embodiments the pharmaceutical preparation comprises at least two active agents. In some embodiments the pharmaceutical preparation comprises at least three active agents. In embodiments comprising more than one active agent, each of the plurality or particles in the preparation may comprise each of the active agents, or the preparation may comprise a plurality of types of particles, each type comprising a different active agent and/or set of active agents.

In some embodiments the pharmaceutical preparation comprises an active agent increases pH. In some embodiments the pharmaceutical preparation comprises an active agent comprises a bicarbonate group. In some embodiments pharmaceutical preparation comprises a bicarbonate salt, such as sodium bicarbonate, potassium bicarbonate, caesium bicarbonate, magnesium bicarbonate, calcium bicarbonate, ammonium bicarbonate, or a mixture thereof.

In some embodiments the pharmaceutical preparation comprises an active agent increases oxygen tension. In some embodiments active agent comprises a peroxide functional group. In some embodiments the active agent comprises hydrogen peroxide. In some embodiments the active agent is hydrogen peroxide. In some embodiments the active agent comprises an organic peroxide. In some embodiments the active agent is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the pharmaceutical preparation comprises an active agent that is an inorganic peroxide. In some embodiments the pharmaceutical preparation comprises an active agent that is carbamide peroxide. In some embodiments the pharmaceutical preparation comprises an active agent that is sodium percarbonate.

In some embodiments the pharmaceutical preparation comprises an active agent that increases production of oxygen from stores in the gut. An example is catalase, a common enzyme found in nearly all living organisms exposed to oxygen. Accordingly, In some embodiments the pharmaceutical preparation comprises an active agent that is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In such embodiments catalase increases oxygen tension by increasing the rate of decomposition of endogenous hydrogen peroxide to water and oxygen. In other embodiments catalase and an active agent that comprises hydrogen peroxide are used together. In such embodiments the catalase increases the rate of production of oxygen from the hydrogen peroxide active agent. In such embodiments the catalase may also act at least in part by increasing production of oxygen from endogenous sources.

In some embodiments the pharmaceutical preparation comprises a first active agent that increases pH and a second active agent that increases oxygen tension. In some embodiments the pharmaceutical preparation comprises a first active agent that increases pH, a second active agent that increases oxygen tension, and a third active agent that increases production of oxygen from endogenous sources. In some embodiments the pharmaceutical preparation comprises a first active agent that increases pH, a second active agent that increases oxygen tension and is a molecule comprising a peroxide functional group, and a third active agent that increases the rate of decomposition of the peroxide functional group to water and oxygen.

In some embodiments the pharmaceutical preparation comprises an active agent that comprises a peroxide functional group. In some embodiments the active agent that comprises a peroxide functional group is hydrogen peroxide. In some embodiments the active agent that comprises a peroxide functional group is carbamide peroxide. In some embodiments the active agent that comprises a peroxide functional group is sodium percarbonate. In some embodiments the pharmaceutical preparation further comprises a peroxide catalyst.

In some embodiments the pharmaceutical preparation comprises an active agent that comprises a bicarbonate group. In some embodiments the active agent that comprises a bicarbonate group is a bicarbonater salt. In some embodiments the active agent that comprises a bicarbonate group is sodium bicarbonate.

In some embodiments the pharmaceutical preparation comprises a first active agent that comprises a peroxide functional group and a second active agent that comprises a bicarbonate group. In some embodiments the first active agent that comprises a peroxide functional group is hydrogen peroxide. In some embodiments the first active agent that comprises a peroxide functional group is carbamide peroxide. In some embodiments the first active agent that comprises a peroxide functional group is sodium percarbonate. In some embodiments the second active agent that comprises a bicarbonate group is a bicarbonater salt. In some embodiments the second active agent that comprises a bicarbonate group is sodium bicarbonate. In some embodiments the pharmaceutical preparation further comprises a peroxide catalyst.

In some embodiments the pharmaceutical preparation is designed to target release of the at least one active agent to the small intestine. In some embodiments the pharmaceutical preparation is designed to target release of the at least one active agent to the proximal small intestine. In some embodiments the pharmaceutical preparation is designed to target release of the at least one active agent to the distal small intestine. In some embodiments the pharmaceutical preparation is designed to target release of the at least one active agent to the ileum. In some embodiments the pharmaceutical preparation is designed to target release of the at least one active agent to the distal ileum.

In some embodiments the pharmaceutical preparation is designed to target release of the at least one active agent to the colon. In some embodiments the pharmaceutical preparation is formulated so that the at least one active agent is released in the distal small intestine. In some embodiments the pharmaceutical preparation is formulated so that the at least one active agent is released in the distal small intestine and the colon. In some embodiments the pharmaceutical preparation is formulated so that the at least one active agent is released in the ileum. In some embodiments the pharmaceutical preparation is formulated so that the at least one active agent is released in the ileum and the colon. In some embodiments the pharmaceutical preparation is formulated so that the at least one active agent is released in the distal ileum. In some embodiments the pharmaceutical preparation is formulated so that the at least one active agent is released in the distal ileum and the colon. In some embodiments the pharmaceutical preparation is formulated so that the at least one active agent is released in the jejunum. In some embodiments the pharmaceutical preparation is formulated so that the at least one active agent is released in the colon.

In some embodiments the core does not comprise an enzyme. In some embodiments the core does not comprise an enzyme that oxidizes ethanol to acetate.

E. Methods of Weight Management

As demonstrated in the examples, the inventor has discovered that administering a pharmaceutical composition of the invention to a subject has a beneficial effect on the colon microbiome of the subject. By increasing the oxygen tension and/or redox potential and/or pH the colon environment is modified such that (1) the relative abundance of bacterial types that promote at least one condition selected from a metabolic disease or disorder (such as obesity), metabolic syndrome, and cardiovascular disease is reduced; and/or (2) the relative abundance of bacterial types that ameliorate at least one condition selected from a metabolic disease or disorder (such as obesity), metabolic syndrome, and cardiovascular disease is increased. It has also been discovered that increasing the oxygen tension and/or redox potential and/or pH in the colon environment of a subject acts to manage the weight of the subject. Without wishing to be bound by theory, it appears that microbiome modifications caused by increasing the oxygen tension and/or redox potential and/or pH of a subject's colon in turn manage the weight of the subject. This dramatic result is surprising and demonstrates unexpected benefits of the invention.

Accordingly, methods of weight management in a subject are also provided. In some embodiments the methods comprise administering an effective amount of a pharmaceutical composition of the invention to the subject to thereby manage the weight of the subject. In some embodiments the weight management comprises at least one of weight loss, maintenance of weight, controlling weight gain, body mass index (BMI) reduction, maintenance of BMI, and controlling BMI gain. In some embodiments the subject is overweight or obese. In some embodiments the subject has at least one weight-related condition. In some embodiments the at least one weight-related condition is selected from a metabolic disease or disorder, metabolic syndrome, and cardiovascular disease. In some embodiments the at least one weight-related condition is selected from hypertension, dyslipidemia, and type 2 diabetes. In some embodiments at least one symptom of the at least one weight-related condition is ameliorated.

In some embodiments administering an effective amount of a pharmaceutical composition of the invention to the subject increases the relative abundance of at least one of aerobic bacteria and facultatively anaerobic bacteria in the microbiota of the colon of the subject. In some embodiments administering the effective amount to the small intestine and/or large intestine of the subject of at least one agent that increases oxygen tension and/or redox potential and/or pH in the colon of the subject increases the relative abundance of bacteria in at least one phylum selected from Proteobacteria, Bacteriodetes, and Verrucomicrobia is increased in the microbiota of the colon of the subject. In some embodiments the relative abundance of bacteria in the phylum Proteobacteria is increased in the microbiota of the colon of the subject. In some embodiments administering an effective amount of a pharmaceutical composition of the invention to the subject decreases the relative abundance of bacteria in the Firmicutes phylum in the microbiota of the colon of the subject. In some embodiments administering an effective amount of a pharmaceutical composition of the invention to the subject of at least one agent that increases oxygen tension and/or redox potential and/or pH in the colon of the subject decreases the relative abundance of bacteria in the Firmicutes phylum in the microbiota of the colon of the subject.

In some embodiments the at least one agent increases oxygen tension and is a peroxide. In some embodiments the at least one agent increases pH and is selected from bicarbonate salts, carbonate salts, bases, and buffers. In some embodiments the at least one agent is a peroxide catalyst. In some embodiments the at least one agent is selected from carbamide peroxide, sodium percarbonate, sodium bicarbonate, and catalase. In some embodiments the method comprises administering a peroxide and catalase to the subject. In some embodiments the peroxide is selected from carbamide peroxide, sodium percarbonate. In some embodiments the method further comprises administering sodium bicarbonate to the subject.

In some embodiments pharmaceutical composition of the invention is administered to the subject without administering an enzyme to the subject. In some embodiments of the methods the effective amount of a pharmaceutical composition of the invention is administered to the subject without administering an enzyme that oxidizes ethanol to acetate to the subject.

In general the pharmaceutical composition of the invention is administered over a dosing period. A dosing period is a span of time during which the active agent is administered to a subject at a regular dosing interval, such as every four hours, every eight hours, every twelve hours, or once a day. The dosing period may comprise one week, two weeks, one month, three months, six months, nine months, or one year. In some embodiments the active agent is administered at least once a day for the dosing period. In some embodiments the active agent is administered at least once every other day for the dosing period. In some embodiments the active agent is administered at least two times a week for the dosing period. In some embodiments the active agent is administered at least three times a week for the dosing period. In some embodiments the active agent is administered at least four times a week for the dosing period. In some embodiments the active agent is administered at least five times a week for the dosing period.

In some embodiments the dosing period is at least 3 days, at least 5 days, at least 1 week, at least 2 weeks, at least 4 weeks, at least 2 months, at least 3 months, at least 6 months, or at least one year. In some embodiments the dosing period is 3 days, 5 days, 1 week, 2 weeks, 4 weeks, 2 months, 3 months, 6 months, or one year. In some embodiments the dosing period is from 3 to 10 days, from 1 to 2 weeks, from 2 to 4 weeks, from 1 to 2 months, from 3 to 6 months, or from 6 to 12 months.

In some embodiments the pharmaceutical composition of the invention is administered for a dosing period and the weight of the subject does not increase during the dosing period. In some embodiments the pharmaceutical composition of the invention is administered for a dosing period and the weight of the subject decreases during the dosing period. In some embodiments the weight of the subject decreases by at least 1%, at least 2%, at least 3%, at least 4%, at least 5%, at least 6%, at least 7%, at least 8%, at least 9%, or at least 10% during the dosing period.

In some embodiments the pharmaceutical composition of the invention is administered for a dosing period and the BMI of the subject does not increase during the dosing period. In some embodiments the pharmaceutical composition of the invention is administered for a dosing period and the BMI of the subject decreases during the dosing period. In some embodiments the BMI of the subject decreases by at least 1%, at least 2%, at least 3%, at least 4%, at least 5%, at least 6%, at least 7%, at least 8%, at least 9%, or at least 10% during the dosing period.

In some embodiments both the weight of the subject and the BMI of the subject do not increase during the dosing period. In some embodiments both the weight of the subject and the BMI of the subject decrease during the dosing period. In some embodiments the weight of the subject and the BMI of the subject independently each decrease by at least 1%, at least 2%, at least 3%, at least 4%, at least 5%, at least 6%, at least 7%, at least 8%, at least 9%, or at least 10% during the dosing period.

In some embodiments in which the subject has at least one weight-related condition the at least one weight-related condition is selected from a metabolic disease or disorder, metabolic syndrome, and cardiovascular disease.

In some embodiments the at least one weight-related condition is metabolic syndrome. In some embodiments the metabolic syndrome is characterized by at least one feature selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least two features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least three features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least four features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation. In some embodiments the metabolic syndrome is characterized by at least five features selected from insulin resistance, central obesity, glucose intolerance, dyslipidemia with elevated triglycerides, low HDL-cholesterol, microalbuminuria, predominance of small dense LDL-cholesterol particles, hypertension, endothelial dysfunction, oxidative stress, and inflammation.

In some embodiments the subject is pre-obese, obese, or morbidly obese. In some embodiments weight management of the pre-obese, obese, or morbidly obese subject results in at least one of inducing weight loss in a pre-obese, obese, or morbidly obese subject; reducing BMI in a pre-obese, obese, or morbidly obese subject; reducing food intake in a pre-obese, obese, or morbidly obese subject; improving glucose homeostasis in a pre-obese, obese, or morbidly obese subject; preventing weight gain and preventing an increase in BMI in a normal, pre-obese, obese, or morbidly obese subject.

In certain embodiments, the pharmaceutical composition of the invention is administered to a subject suffering from obesity (e.g., a pro-obese, obese, or morbidly obese patient), an obesity-related disease or disorder, diabetes, insulin-resistance syndrome, lypodystrpohy, nonalcoholic steatohepatitis, a cardiovascular disease, polycystic ovary syndrome, or a metabolic syndrome.

In some embodiments the at least one condition is cardiovascular disease.

In some embodiments the at least one condition is type-II diabetes.

Administering an effective amount to the small intestine and/or large intestine of the subject of at least one agent that increases oxygen tension and/or redox potential and/or pH may be achieved using any suitable method. Generally, it will be preferable to provide the at least one active agent in the form of an oral dosage form, including for example any of the oral dosage forms disclosed herein. The oral dosage form is provided orally to the subject and then passes through the stomach to provide the at least one active agent to the small intestine and/or large intestine of the subject. However, alternative approaches may also be used. For example, a feeding tube may be placed to provide a composition comprising the at least one active agent directly to the small intestine or the large intestine. If an oral dosage form is used, any oral dosage form of this disclosure may be used, or any other suitable oral dosage form known in the art.

In some embodiments the methods comprise administering no more than one active agent. In some embodiments the methods comprise administering at least two active agents. In some embodiments the methods comprise administering at least three active agents. In some embodiments of the methods a single oral dosage form is administered, which may comprise a plurality of active agents. In other embodiments a plurality of oral dosage forms is administered, which may each comprise a different active agent or different combination of active agents.

In some embodiments the methods comprise administering an active agent that increases pH. In some embodiments the methods comprise administering an active agent that comprises a bicarbonate group and/or a carbonate group. In some embodiments the methods comprise administering an active agent that comprises a bicarbonate salt, such as without limitation sodium bicarbonate, potassium bicarbonate, caesium bicarbonate, magnesium bicarbonate, calcium bicarbonate, ammonium bicarbonate, or a mixture thereof.

In some embodiments the methods comprise administering an active agent that comprises a carbonate salt. In some embodiments the methods comprise administering an active agent that comprises a base. In some embodiments the methods comprise administering an active agent that comprises a buffer.

In some embodiments the methods comprise administering an active agent that increases oxygen tension. In some embodiments the methods comprise administering an active agent that comprises a peroxide functional group. In some embodiments the methods comprise administering an active agent that comprises hydrogen peroxide. In some embodiments the methods comprise administering an active agent that is hydrogen peroxide. In some embodiments at least one agent is hydrogen peroxide. In some embodiments the at least one peroxide is an organic peroxide. In some embodiments the at least one peroxide is an organic peroxide selected from acetyl acetone peroxide, acetyl benzoyl peroxide, ascaridole, benzoyl peroxide, di-(1-naphthoyl)peroxide, diacetyl peroxide, ethyl hydroperoxide, ergesterol peroxide, iodoxy compounds, methyl isobutyl ketone peroxide. In some embodiments the at least one agent is an inorganic peroxide. In some embodiments the at least one agent is an inorganic peroxide selected from Ammonium persulfate, Calcium peroxide, Magnesium peroxide, Potassium persulfate, Sodium perborate, and Sodium percarbonate. In some embodiments the at least one agent is carbamide peroxide. In some embodiments the at least one agent is Sodium percarbonate. In some embodiments the methods comprise administering an active agent that is carbamide peroxide. In some embodiments the methods comprise administering an active agent that is Sodium percarbonate.

In some embodiments the the methods comprise administering an active agent that increases production of oxygen from stores in the gut and/or added stores. In some embodiments the agent that increases production of oxygen from stores in the gut and/or added stores is an organic peroxide catalyst or an inorganic peroxide catalyst. An example is catalase, a common enzyme found in nearly all living organisms exposed to oxygen. Accordingly, In some embodiments the methods comprise administering an active agent that is a catalase. In some embodiments the catalase is a human catalase. In some embodiments the catalase is a non-human catalase. In some embodiments the catalase is a mammalian catalase. In some embodiments the catalase is a non-mammalian catalase. In some embodiments the catalase is used as the only agent that increases oxygen tension. In such embodiments catalase increases oxygen tension by increasing the rate of decomposition of endogenous hydrogen peroxide to water and oxygen. In other embodiments of the methods, catalase and an active agent that comprises hydrogen peroxide are used together. In such embodiments the catalase increases the rate of production of oxygen from the hydrogen peroxide active agent. In such embodiments the catalase may also act at least in part by increasing production of oxygen from endogenous sources.

In some embodiments the methods comprise administering a first active agent that increases pH and a second active agent that increases oxygen tension. In some embodiments the methods comprise administering a first active agent that increases pH, a second active agent that increases oxygen tension, and a third active agent that increases production of oxygen from endogenous sources. In some embodiments the methods comprise administering a first active agent that increases pH, a second active agent that increases oxygen tension and is a molecule comprising a peroxide functional group, and a third active agent that increases the rate of decomposition of the peroxide functional group to water and oxygen.

In some embodiments the methods comprise administering an active agent that comprises a peroxide functional group. In some embodiments the active agent that comprises a peroxide functional group is hydrogen peroxide. In some embodiments the active agent that comprises a peroxide functional group is carbamide peroxide. In some embodiments the pharmaceutical preparation further comprises a peroxide catalyst.

In some embodiments the methods comprise administering an active agent that comprises a carbonate group or a bicarbonate group. In some embodiments the active agent that comprises a bicarbonate group is a carbonate salt or a bicarbonate salt. In some embodiments the active agent that comprises a bicarbonate group is sodium bicarbonate. In some embodiments the active agent that comprises a carbonate group is sodium carbonate.

In some embodiments the methods comprise administering a first active agent that comprises a peroxide functional group and a second active agent that comprises a bicarbonate group. In some embodiments the first active agent that comprises a peroxide functional group is hydrogen peroxide. In some embodiments the first active agent that comprises a peroxide functional group is carbamide peroxide. In some embodiments the second active agent that comprises a bicarbonate group is a bicarbonater salt. In some embodiments the second active agent that comprises a bicarbonate group is sodium bicarbonate. In some embodiments the pharmaceutical preparation further comprises a peroxide catalyst.

The "effective amount" of the active agent(s) that is administered may be determined experimentally using methods that are standard in the art. For example, the methods described in the examples may be employed in mice and/or humans to identify an active agent and/or to perform a dose-ranging study to define the range of amounts of the active agent(s) that provide a desired benefit and/or the lowest dose that provides a desired benefit.

For agents that increase oxygen tension a dose range of 0.1 ng/kg to 1 g/kg may, for example, be tested in the mouse model to identify a therapeutically effective amount. For candidate agents that increase pH a dose range of 0.1 microgram/kg to 10 g/kg may, for example, be tested in the mouse model to identify a therapeutically effective amount.

Carbamide peroxide is used at a dose of from 1 ng/kg to 100 mg/kg per day, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments carbamide peroxide is used at a dose of at least 25 mg three times per day. In some embodiments carbamide peroxide is used at a dose of at least 50 mg three times per day. In some embodiments carbamide peroxide is used at a dose of at least 75 mg three times per day. In some embodiments carbamide peroxide is used at a dose of at least 100 mg three times per day.

Sodium percarbonate is used at a dose of from 1 ng/kg to 100 mg/kg, such as from 1 ng/kg to 10 ng/kg, from 10 ng/kg to 100 ng/kg, from 1 microgram/kg to 10 micrograms/kg, from 10 microgram/kg to 100 micrograms/kg, from 100 microgram/kg to 1 mg/kg, from 1 mg/kg to 10 mg/kg, or from 10 mg/kg to 100 mg/kg, or at a dose that is bounded by any combination of two of these recited endpoints or at a dose of at least one of these endpoints. The dose is administered 1, 2, 3, 4, 5, 6, 7, 8, 9, or 10 times per day. In a preferred embodiment the dose is administered 3 times per day.

In some embodiments sodium percarbonate is used at a dose of at least 25 mg three times per day. In some embodiments sodium percarbonate is used at a dose of at least 50 mg three times per day. In some embodiments sodium percarbonate is used at a dose of at least 75 mg three times per day. In some embodiments sodium percarbonate is used at a dose of at least 100 mg three times per day.

In some embodiments the active agent comprises hydrogen peroxide and the agent is administered to a subject at a dose of from 0.01 mg to 100 mg of hydrogen peroxide equivalent. In some embodiments the active agent is administered at a dose of from 0.1 mg to 5 mg of hydrogen peroxide equivalent. In some embodiments the active agent is administered at a dose of from 5 mg to 10 mg of hydrogen peroxide equivalent. In some embodiments the active agent is administered at a dose of from 10 mg to 20 mg of hydrogen peroxide equivalent. In some embodiments the active agent is administered at a dose of from 20 mg to 40 mg of hydrogen peroxide equivalent. In some embodiments the active agent is administered at a dose of from 40 mg to 60 mg of hydrogen peroxide equivalent. In some embodiments the active agent is administered at a dose of from 60 mg to 80 mg of hydrogen peroxide equivalent. In some embodiments the active agent is administered at a dose of from 80 mg to 100 mg of hydrogen peroxide equivalent.

In some embodiments the active agent is administered at a dose of from 100 mg to 1 g of hydrogen peroxide equivalent. In some embodiments the active agent is administered at a dose of from 100 mg to 200 mg of hydrogen peroxide equivalent. In some embodiments the active agent is administered at a dose of from 200 mg to 400 mg of hydrogen peroxide equivalent.

Sodium bicarbonate is used at a dose of from 1 microgram/kg to 1 g/kg, such as at 1 microgram/kg to 10 micrograms, from 10 micrograms/kg to 100 micrograms/kg, from 100 micrograms/kg to 1 mg/kg, from 1 mg/kg to 10 mg/kg, from 10 mg/kg to 100 mg/kg, or 100 mg/kg to 1 g, or at a dose that is bounded by any combination of two of these recited endpoints or at a dose of at least one of these endpoints.

Catalase is used at a dose of from 0.0001 to 10,000 Baker's units per kg, such as from 0.0001 to 0.001 Baker's units per kg, from 0.001 to 0.01 Baker's units per kg, from 0.01 to 0.1 Baker's units per kg, from 0.1 to 1 Baker's units per kg, from 1 to 10 Baker's units per kg, from 10 to 100 Baker's units per kg, from 100 to 1,000 Baker's units per kg, or from 1,000 to 10,000 Baker's units per kg. The dose is administered 1, 2, 3, 4, 5, 6, 7, 8, 9, or 10 times per day. In a preferred embodiment the dose is administered 3 times per day.

In some embodiments catalase is used at a dose of at least 25 mg three times per day. In some embodiments catalase is used at a dose of at least 50 mg three times per day. In some embodiments catalase is used at a dose of at least 75 mg three times per day. In some embodiments catalase is used at a dose of at least 100 mg three times per day.

In some embodiments the active agent is administered on an empty stomach. In other embodiments the active agent is administered with food. In some embodiments the active agent is administered with meals.

In some embodiments of the methods the microbiota profile of the colon of the subject is modulated as a result of the treatment. In some embodiments administering the effective amount of the at least one agent to the small intestine and/or large intestine of the subject modulates the microbiota profile of the large intestine of the subject.

In some embodiments the relative abundance of at least one of aerobic bacteria and facultatively anaerobic bacteria is increased in the microbiota of the colon of the subject. In some embodiments the relative abundance of bacteria in at least one phylum selected from Proteobacteria, Bacteriodetes, and Verrucomicrobia is increased in the microbiota of the colon of the subject. In some embodiments the relative abundance of bacteria in the Proteobacteria phylum is increased in the microbiota of the colon of the subject. In some embodiments the relative abundance of bacteria in the Firmicutes phylum is decreased in the microbiota of the colon of the subject. In some embodiments the relative abundance of bacteria in at least one phylum selected from Proteobacteria, Bacteriodetes, and Verrucomicrobia is increased in the microbiota of the colon of the subject; and the relative abundance of bacteria in the Firmicutes phylum is decreased in the microbiota of the colon of the subject.

In some embodiments the relative abundance of at least one class of bacteria selected from Gammaproteobacteria, Alphaproteobacteria and Bacteriodetes is increased in the microbiota of the colon of the subject. In some embodiments the relative abundance of at least one class of bacteria selected from Clostridia, Erysipelotrichia, and Bacilli is decreased in the microbiota of the colon of the subject. In some embodiments the relative abundance of at least one class of bacteria selected from Gammaproteobacteria, Alphaproteobacteria and Bacteriodetes is increased in the microbiota of the colon of the subject; and the relative abundance of at least one class of bacteria selected from Clostridia, Erysipelotrichia, and Bacilli is decreased in the microbiota of the colon of the subject.

In some embodiments the relative abundance of at least one order of bacteria selected from Enterobacteriales, Bacteriodales, and Verrucomicrobiales is increased in the microbiota of the colon of the subject. In some embodiments the relative abundance of at least one order of bacteria selected from Clostridiales, Erysiopelotrichales, and Lactobacillales is decreased in the microbiota of the colon of the subject. In some embodiments the relative abundance of at least one order of bacteria selected from Enterobacteriales, Bacteriodales, and Verrucomicrobiales is increased in the microbiota of the colon of the subject; and the relative abundance of at least one order of bacteria selected from Clostridiales, Erysiopelotrichales, and Lactobacillales is decreased in the microbiota of the colon of the subject.

In some embodiments the relative abundance of at least one family of bacteria selected from Enterobacteriaceae and Bacteroidaceae is increased in the microbiota of the colon of the subject. In some embodiments the relative abundance of at least one family of bacteria selected from Erysiopelotrichaceae, Prevotellaceae, Coriobacteriaceae, and Alcaligenaceae is decreased in the microbiota of the colon of the subject. In some embodiments the relative abundance of at least one family of bacteria selected from Enterobacteriaceae and Bacteroidaceae is increased in the microbiota of the colon of the subject; and the relative abundance of at least one family of bacteria selected from Erysiopelotrichaceae, Prevotellaceae, Coriobacteriaceae, and Alcaligenaceae is decreased in the microbiota of the colon of the subject.

In some embodiments the relative abundance of at least one genus of bacteria selected from *Escherichia, Bacteriodes, Alistipes*, and *Akkermansia* is increased in the microbiota of the colon of the subject. In some embodiments the relative abundance of at least one genus of bacteria selected from *Clostridium* and *Lactobacillus* is decreased in the microbiota of the colon of the subject. In some embodiments the relative abundance of at least one genus of bacteria selected from *Escherichia, Bacteriodes, Alistipes*, and *Akkermansia* is increased in the microbiota of the colon of the subject; and the relative abundance of at least one genus of bacteria selected from *Clostridium* and *Lactobacillus* is decreased in the microbiota of the colon of the subject.

In some embodiments the relative abundance of *Akkermansia muciniphila* is increased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject. In some embodiments the relative abundance of at least one type of bacteria selected from Firmicutes (Clostridia), Erysiopelotrichaceae is decreased in the microbiota of the colon of the subject.

In some embodiments the relative abundance of at least one type of bacteria selected from Gammaproteobacteria, Alphaproteobacteria, Enterobacteriaceae (e.g., *Escherichia*), Bacteriodetes, and Verrucomicrobia (e.g., *Akkermansia*) is increased in the microbiota of the colon of the subject; and the relative abundance of at least one type of bacteria selected from Firmicutes (Clostridia), Erysiopelotrichaceae is decreased in the microbiota of the colon of the subject.

In some embodiments the methods further comprise collecting a stool sample from the subject and assaying the microbiota profile in the stool sample to determine the relative abundance of at least one phylum of bacteria selected from Proteobacteria, Bacteriodetes, Verrucomicrobia, and Firmicutes; and/or to determine the relative abundance of at least one class of bacteria selected from Gammaproteobacteria, Alphaproteobacteria, Bacteriodetes, Clostridia, Erysipelotrichia, and Bacilli; and/or to determine the relative abundance of at least one order of bacteria selected from Enterobacteriales, Bacteriodales, Verrucomicrobiales, Clostridiales, Erysiopelotrichales, and Lactobacillales; and/or to determine the relative abundance of at least one family of bacteria selected from Enterobacteriaceae, Bacteroidaceae, Erysiopelotrichaceae, Prevotellaceae, Coriobacteriaceae, and Alcaligenaceae; and/or to determine the relative abundance of at least one genus of bacteria selected from *Escherichia, Bacteriodes, Alistipes, Akkermansia, Clostridium*, and *Lactobacillus*; and/or to determine the relative abundance of *Akkermansia muciniphila*. In some embodiments the stool sample is collected at least one time point selected from before initiation of administering at least one agent that increases oxygen tension and/or redox potential and/or pH, during a course of administering at least one agent that increases oxygen tension and/or redox potential and/or pH, and after completion of administering a course of at least one agent that increases oxygen tension and/or redox potential and/or pH.

In some embodiments in which the relative abundance of a type of bacteria is increased in the colon of the subject the increase in relative abundance is at least 25%, at least 50%, at least 75%, at least 100% (i.e., one fold), at least 200% (i.e., two fold), at least 300%, at least 400%, at least 500%, at least 600%, at least 700%, at least 800%, at least 900%, at least 1,000% (i.e., ten fold), or at least 10,000% (i.e., 100 fold). In some embodiments in which the relative abundance of a type of bacteria is decreased in the colon of the subject the decrease in relative abundance is at least 10%, at least 25%, at least 50%, at least 75%, at least 90% (i.e., ten fold), at least 95% (i.e., 20 fold), at least 99% (i.e., 100 fold), at least 99.9% (i.e., 1000 fold).

In some embodiments of the methods the at least one agent that increases oxygen tension and/or redox potential and/or pH in the colon of a subject is administered to the subject without administering an enzyme to the subject. In some embodiments of the methods the at least one agent that increases oxygen tension and/or redox potential and/or pH in the colon of a subject is administered to the subject without administering an enzyme that oxidizes ethanol to acetate to the subject.

EXAMPLES

The examples are provided to further define the disclosure without, however, limiting the disclosure to the specifics of these examples.

Example 1

Pharmaceutical Preparations

A multiparticulate formulation composed of 3 components was formed, namely a core particle (~1 mm diameter) containing the API, a subcoat layer to create a barrier between the functional (enteric) coating and the API, and finally the functional coating as the outmost layer, which is an enteric coating designed to target the release of API to the distal small intestine/proximal colon region.

Core API particle: Sodium percarbonate (Provox C, OCI Chemical Corporation).

Subcoat: HPMC layer.

Enteric coating: Eudragit FS30D.

Sodium percarbonate particles were coated first with a subcoat layer of HPMC. Next, the particles having the subcoat were coated with HPMC (5% weight gain), and then coated with the Eudagrit FS3OD (35% weight gain).

Methods

Sodium percarbonate particles were prepared by sieving using a 0.6 mm sieve under dry conditions.

The HPMC layer coating solution in ddH$_2$O was prepared as follows using Hypromellose USP PHARMACOAT 606 (LOT No. 5118397) and Super Refined PEG 400-LQ-(MH), SR40377 (LOT No. 0000608682). Briefly, 30.0 g HPMC (7.5% w/w) and 3.0 g (0.75% w/w) PEG 400 were dissolved in 400 g water.

Enteric coating layer solution in ddH$_2$O was prepared using the following materials: EUDRAGIT® FS 30 D (LOT No. B15065004), Talc USP (LOT No. 2DK0194), H$_2$O: Milli-Q, Triethyl citrate USP-NF (LOT No. 6P013354), Glyceryl Monostearate NF (LOT No. 127309), and Polysorbate 80 NF (LOT No. 2FB0143).

Two enteric coating formulas were prepared and tested. Formula 1: EUDRAGIT® FS 30D—250 g, Talc—37.5 g, H$_2$O 275-g, total=562.5 g total. Formula 2: EUDRAGIT® FS 30D—298.9 g, Polysorbate 80 (33%)—4.4 g, Triethyl citrate—4.5 g, GMS—3.6 g, H$_2$O—188.7 g=500 g total.

In each case the coating solution was passed through a 0.25 mm sieve and continuously stirred using a magnetic stirrer during the coating process to prevent the solids from settling.

The sodium percarbonate particles were coated with an HPMC layer using a fluid bed having the following settings: Preheating temperature (° C.)—45, Atomizing pressure—1.5-2, Outlet air temperature—40-45, Drying temperature—42, Capacity of fan—8-9, Pump speed (rpm)—1.6-2.5. Sodium percarbonate particles were sieved using a 0.6 mm sieve before coating. Particles larger than 0.6 mm were collected. Particle weight gain after sealing layer coating was ~5.0%.

The sealed sodium percarbonate particles were coat sealed with a EUDRAGIT® FS 30 D layer using a fluid bed having the following settings: Preheating temperature (° C.)—40, Atomizing pressure—1.5-2, Outlet air temperature—38-42, Drying temperature—40, Capacity of fan—8-9, Pump speed (rpm)—1.6-2.5.

Weight gain after enteric coating (Formula #1: FS30D+ Talc): 6.8%, 12.7%, 20.3%, 35.0%, 50.0%. Weight gain after enteric coating (Formula #2: FS30D+GMS): 24.9%. Size of coated particles was between 0.9 mm and 1.18 mm. Average weight of each coated particle was 0.96±0.07 mg (N=10). 35.0% and 50.0% weight gain particles are filled into size 3 HPMC capsules (CAPSUGEL, Vcaps Plus Hypromellose Capsules) (200 mg/capsules) for further testing.

Results

A two-stage dissolution test was used. Stage 1: 0.1 M HCl (pH 1.2) for 2 hours, Stage 2: 0.2 M PBS (pH 7.4) until dissolved, Paddle speed: 100 rpm, Volume: 500 mL, Temperature: 37° C. Three individual vessels were used for each sample (~1 g particles/vessel). Enteric coating dissolution was determined visually by presence or absence of gas bubble release from the particles.

Formula #1 was evaluated with two enteric coating levels: 6.8% weight gain and 12.7% weight gain. Neither remained stable in 0.1 M HCl for 2 hours. But the 12.7% weight gain samples exhibited longer stability in acid.

The coating level was to ~20.0% and the two enteric coating formulations were compared. Stability in acid was significantly improved. Formula #1 showed better acid stability than Formula #2. After changing medium to 0.2 M PBS (pH 7.4), coated particles dissolved within 10 minutes.

Next enteric coating level using Formula #1 was increased to 35% and 50%. Both coating levels protected API in 0.1 M HCl, with no dissolution observed. Although at 35% coating level, several particles started to flow on the surface of the dissolution medium after 1 hour. After changing to 0.2 M PBS (pH 7.4), both groups of coated particles started to dissolve within 15 minutes. Slight delay was observed in the 50% coating group. Completion of dissolution was noticed after 1 hour.

Due to the existence of Talc in formulation #1, dissolution medium became turbid afterwards. The dissolution process proceeded as follows: particles first started to float on the medium surface, bubbles were observed on the surface of the coated particles as well as in the medium. Afterwards, more bubbles formed and dissolution medium started turning turbid. Finally, all of the coated particles lost the rigid round shape and completely dissolved in PBS.

In vitro results for Formula #1 showed good enteric properties and successful release at pH 7.4, indicating its suitability for use in vivo.

In the following examples a formulation using 35% coating level version of Formula #1 was used, as it showed good enteric properties.

Example 2

Methods of Weight Management

Methods

Three subjects participated in the study. The study followed an adaptive trial design with dynamic dose adjustment. Subject 1 was a 57-year-old female with a baseline body-mass index (BMI) of 23.6; Subject 2 was a 56-year-old male with a baseline BMI of 27.9; and Subject 3 was a 33-year-old male with a baseline BMI of 37.1. Dose range was 1-3 mg/kg/day. Baseline anthropometric and clinical parameters for study subjects are outlined in Table 1.

TABLE 1

Anthropometric and clinical parameters

| | Subject #1 | Subject #2 | Subject #3 |
| --- | --- | --- | --- |
| Age, years | 57 | 56 | 33 |
| Gender, F/M | F | M | M |
| BMI, baseline, kg/m2 | 23.6 | 27.9 | 37.1 |
| Weight, baseline, kg | 60.5 | 90.4 | 131 |

Subjects were weight stable for at least three months prior to dosing. Subjects were not on any medications before (up to 1 month) or during dosing. Table 2 describes the pill-dosing regimen used for each subject. Dose values indicate API amount.

TABLE 2

Dosing regimen

| | Subject #1 | Subject #2 | Subject #3 |
| --- | --- | --- | --- |
| Time period | Day 0-36 | Day 0-10 | Day 0-6 |
| Dose frequency | QD | QD | BID |
| Dosing times | AM | AM | AM/PM |
| Dose per administration, mg | 100 | 100 | 100 |
| Total daily dose, mg | 100 | 100 | 200 |
| Total daily dose bw adj., mg/kg | 1.67 | 1.11 | 1.53 |
| Time period | — | Day 11-21 | Day 7-14 |
| Dose frequency | — | BID | QID |
| Dosing times | — | AM/PM | Every 6 hours |
| Dose per administration, mg | — | 100 | 100 |
| Total daily dose, mg | — | 200 | 400 |
| Total daily dose bw adj., mg/kg | — | 2.22 | 3.05 |
| Time period | — | Day 22-34 | Day 15-36 |
| Dose frequency | — | QD | BID |
| Dosing times | — | AM | AM/PM |
| Dose per administration, mg | — | 200 | 200 |
| Total daily dose, mg | — | 200 | 400 |
| Total daily dose bw adj., mg/kg | — | 2.22 | 3.05 |
| Total dosing period, days | 36 | 34 | 36 |

Subjects were instructed to continue ad libitum diet during dosing (no change in daily food intake, same as baseline) and they were instructed not to exercise in addition to their daily activities. Subjects were also instructed not to consume any alcohol during dosing period.

Figure 2:
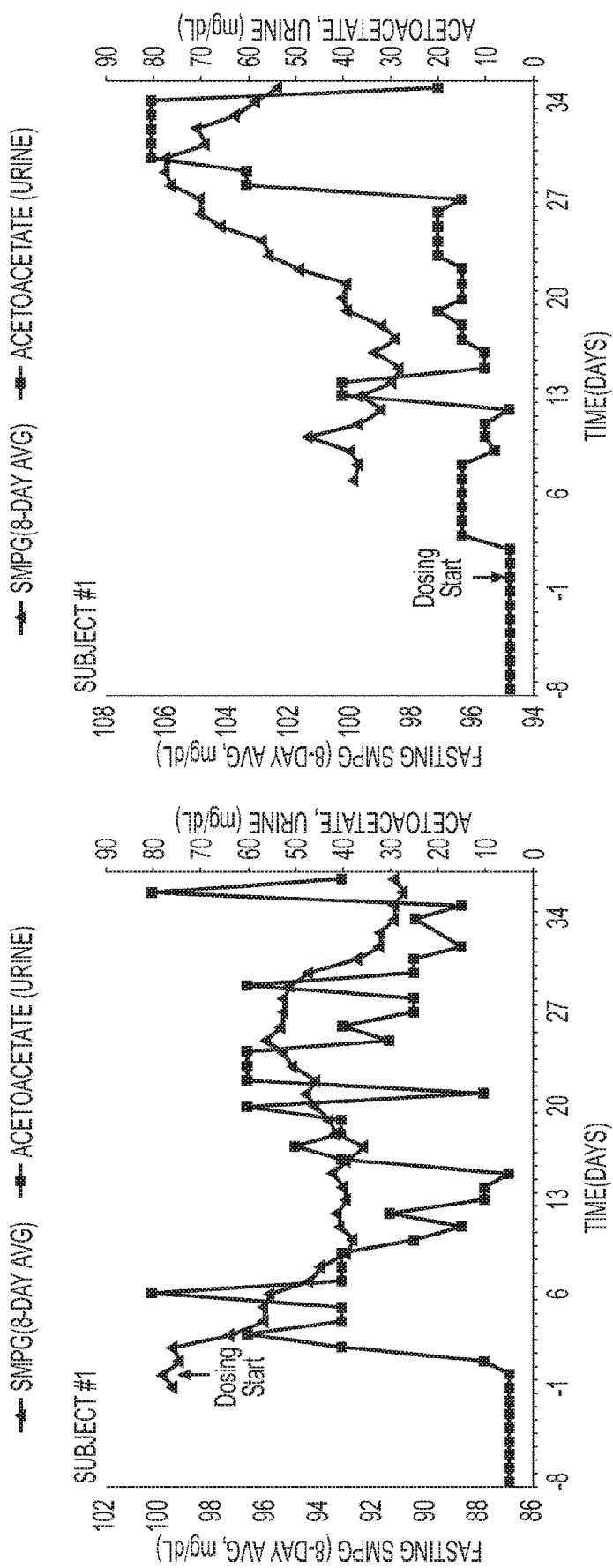
FIG. 2 shows fasting SMPG and urine ketone results for subjects 1 and 2. Each fasting SMPG data point indicates the average of plasma glucose measurements over the previous 8-days.

Fasting blood glucose measurements: Fasting self-measured plasma glucose (SMPG) measurements were taken daily in the mornings. In FIG. 2, each daily data point for SMPG indicates the average of daily SMPG measurements over the previous 8 days. Subject #1 had 8 baseline data points for SMPG and subject #2 and #3 had only 1 baseline data point. Only subjects #1 and #2 consistently performed SMPG measurements during dosing period.

Urine ketone measurements: Subjects performed daily urine ketone measurements using color indicator ketone strips (TRUEplus ketone strips), which measure urine acetoacetate concentration (mg/dL). Each measurement was recorded against the reference color scale and photographed for independent scoring and future reference.

Serum metabolic marker measurements: Subjects #1 and #2 had venous blood drawn at a medical center at dosing day 28 and sampled blood was analyzed for clinical parameters (liver, cholesterol, glucose metabolism, thyroid hormones etc) as listed in Table 3.

TABLE 3

Metabolic data

| | Subject #1 | Subject #2 | Subject #3 |
|---|---|---|---|
| Body weight, % change | −5.29% | −4.76% | −6.03% |
| Absolute change, kg | −3.2 | −4.3 | −7.9 |
| Baseline, kg | 60.5 | 90.4 | 131 |
| Dose end, kg | 57.3 | 86.1 | 123.1 |
| BMI, absolute change, kg/m2 | −1.3 | −1.3 | −2.2 |
| Baseline, kg/m2 | 23.6 | 27.9 | 37.1 |
| Dose end, kg/m2 | 22.4 | 26.6 | 34.8 |
| % Excess weight loss, day 36 | −46% | −29% | −16% |
| SMPG, 8-day avg, % change | −8.74% | 2.40% | — |
| Absolute change, mg/dL | −8.7 | 2.4 | — |
| Baseline, mg/dL | 99.5 | 99.9 | 201 |
| Dose end, mg/dL | 90.8 | 102.3 | — |
| Fasting insulin, day 28, uU/mL | 3 | 9.7 | — |
| HbA1c (%), day 28 | 5.3 | 5.2 | — |
| HOMA-IR, day 28 | 0.6 | 2.5 | — |
| ALT, day 28 | 13 | 20 | — |
| AST, day 28, U/L | 14 | 18 | — |
| ALP, day 28 | 45 | 44 | — |
| Bilirubin, day 28, mg/dL | 0.48 | 0.75 | — |
| GGT, day 28, U/L | 20 | 15 | — |
| T3 Free, day 28, pg/mL | 2.19 | — | — |
| T4 Free, day 28, ng/dL | 1.16 | — | — |
| TSH, day 28, mIU/L | 1.76 | — | — |
| Triglycerides, day 28, mg/dL | 68 | 85 | — |
| HDL, day 28, mg/dL | 89 | 56 | — |
| LDL, day 28, mg/dL | 129 | 110 | — |
| Total cholesterol, day 28, mg/dL | 232 | 183 | — |

Results

Figure 4:
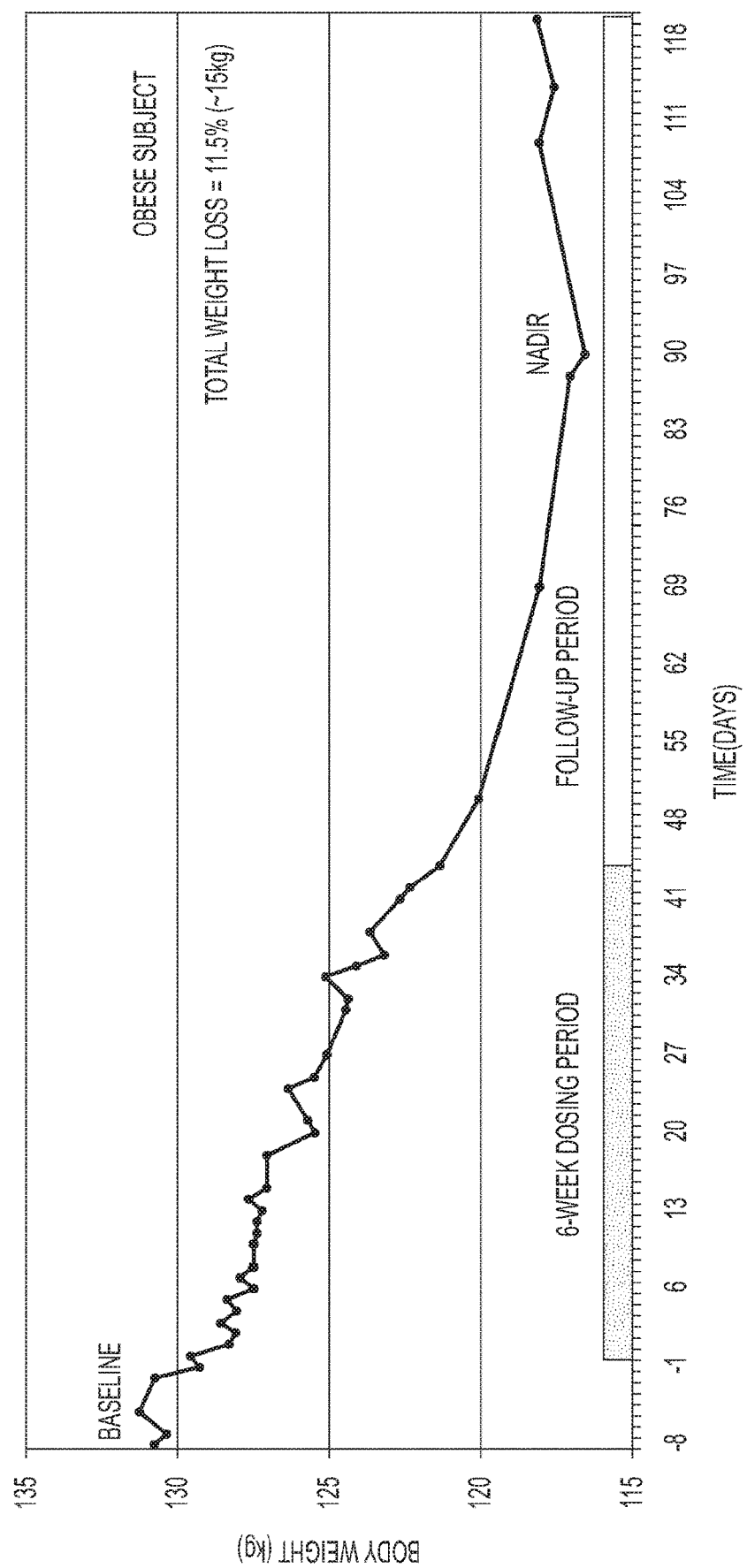
FIG. 4 shows additional body weight data for subject 3.

Body weight decreased substantially in all subjects after 5-6 weeks of dosing (−5.36% mean change from baseline, −5.1 kg mean absolute change, 16-46% excess weight loss, Table 3). Each subject's body weight over time is plotted in FIG. 1. These results are on par with efficacy of gastric bypass surgery (10-15% EWL/month, 4-5 kg/month) (1, 2). The substantial weight loss of ~15 kg (~33 lbs; 11.5% loss from baseline) through the follow-up period in subject #3 (FIG. 4), who is a potential candidate for bariatric surgery, is particularly noteworthy. Based on self-reporting of all subjects, the pattern of weight loss was not attributable to changes in dietary habits (i.e., no change in absolute food intake or food choice).

Food Intake and Hunger: Throughout dosing period, food intake or food preference reported by subjects did not change significantly and was similar to baseline (data not shown). Subjects reported loss of appetite in the first few days at the start of dosing but their appetite returned to normal thereafter. Self reported hunger levels (average of last 2 days, on a 1-10 visual scale (3)) decreased relative to baseline towards the end of dosing (baseline: 5.6 (0.7), end of dosing: 3.7 (0.4)).

Figure 3:
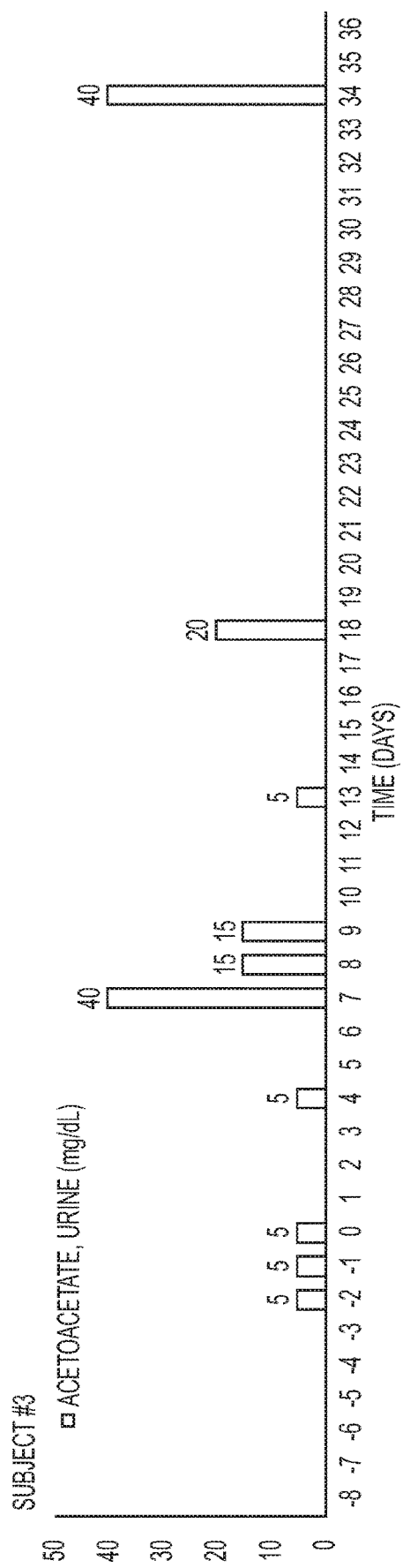
FIG. 3 shows urine ketone results for subject 3. Urine ketone levels (acetoacetate) increased in subject 3 during dosing as measured by standard urine ketone strips.

Metabolic Parameters: All the metabolic data is summarized in Table 3. FIG. 2 shows self-measured plasma glucose (SMPG) (8-day average) and urine ketone results for subjects #1 and #2. FIG. 3 shows urine ketone results for subject #3 over dosing period. Subject #1 had a decrease in SMPG compared to baseline at end of dosing, whereas subject #2 had a slight increase. All subjects experienced substantial increase in ketone body excretion in urine during dosing period indicating ketogenesis, fat mobilization and fat oxidation. Urine and serum ketones also increase dramatically in the early post-operative period (0-6 months) after RYGB (4, 5).

All subjects experienced significant increases in ketone body excretion in urine as measured by in-home urinalysis (TRUEplus™ ketone strips) during the dosing period indicating induction of ketogenesis (i.e., physiological ketosis), fat mobilization and fat oxidation. Of note, urine and serum ketones also increase dramatically in the early post-operative period (0-6 months) after RYGB surgery. (14, 15) 16S rRNA sequencing of fecal samples was also performed in Subject #3 using a microbiome sampling kit (OMNIgene-Gut, DNA Genotek). The results showed that relative abundance of Proteobacteria increased to 6.14% (day 3 of doing) from 3.73% (baseline) in Subject #3.

The original test plan was simply to gather an initial understanding of tolerability and potential efficacy. Therefore, no baselines were taken for other measures besides weight. However, the 5.4% reduction in weight following 28 days allowed for a unique opportunity to assess some other measures in an antidotal manner. Two of the non-obese test subjects submitted themselves for the testing of liver markers (ALT, AST, ALP, GGT, Bilirubin) on dosing day 28. The results were within normal range, indicating favorable liver safety profile (Table 3). Fasting insulin levels were 3 and 9.7 uU/mL for subjects #1 and #2 respectively.

LDL cholesterol was in the high range (>100 mg/dL) in both subjects, which could be due to active fat mass loss and fat mobilization into serum (6, 7), which is also supported by constantly high urine ketone levels independent of food intake (FIGS. 2,3). These results are consistent with low fasting insulin levels measured at day 28 (Table 3) (8). In particular, subject #1 had extremely low insulin levels compared to average female in the same BMI range (3 uU/mL vs 6-8 uU/mL) (9). After RYGB, insulin levels also rapidly fall and insulin resistance resolves (10, 11).

Though no direction of change could be determined due to a lack of baseline measurements for these markers, the high range of the LDL-c levels may suggest that active fat mobilization caused a transient increase in this marker. This is consistent with a phenomenon that has been reported in non-obese subjects during weight loss. (16, 17) This state of fat mobilization is also in line with constantly high urine ketone levels independent of food intake observed in our test subjects. These results are also consistent with relatively low range fasting insulin levels measured at day 28 in the study group and as previously demonstrated during weight loss. (18) Further to this hypothesis, after RYGB, insulin levels also rapidly fall and insulin resistance resolves. (19, 20)

The most frequent AEs were constipation, dry mouth, metallic taste in mouth, burnt sensation on tongue, loss of appetite and increased thirst & water consumption. All AEs, except constipation and increased water consumption, resolved after the first 1-2 weeks of dosing. These AEs are consistent with a prolonged ketosis state achieved during dosing, as fasting or low carb diet induced ketosis also produces similar side effects (12). In particular, metallic taste in mouth during ketosis is believed to be a result of a ketone body acetone being excreted into the mouth during ketosis. There were no significant AE frequency or severity differences between dosing levels or subjects Discussion This proof-of-concept clinical trial tested the safety, tolerability, and weight-reducing effects of a novel oral formulation designed to mimic the mechanism of action of gastric bypass surgery. The formulation appeared to be safe over 5 weeks of dosing with minor side effects. The rate and extent of weight loss, and metabolic data reported in this study should be contextualized. The minimum clinically significant weight loss after 1 year of therapy (behavioral modification and/or medication) is often regarded as 3-5%, assuming risk factors such as waist circumference, blood pressure, serum lipids and inflammatory markers also improve. In fact, the US FDA has set 5% total bodyweight loss at 1 year as a clinical efficacy hurdle for marketing approval of drugs intended to treat obesity. In the current study, our formulation resulted in profound body weight loss of approximately 5-6% (16-46% EWL) at 5 weeks. Remarkably, the observed weight loss was achieved with no significant change in food intake, suggesting increased basal energy expenditure. These results are in line with the efficacy of bariatric surgery. RYGB patients usually lose 4-5% of body weight (10-20% EWL) in the first month on a very low calorie diet (300-600 kcal/day). A large fraction of this initial weight loss is actually due to the trauma of the surgery and includes significant lean mass loss (1, 2). We also observed rapid appearance and sustained presence of ketone bodies in urine despite relatively constant food intake. This observation strongly suggests dosing-induced drop in basal insulin levels and subsequent fat mobilization, lipolysis and fat oxidation (13).

Example 3

Methods of Weight Management

Figure 5:
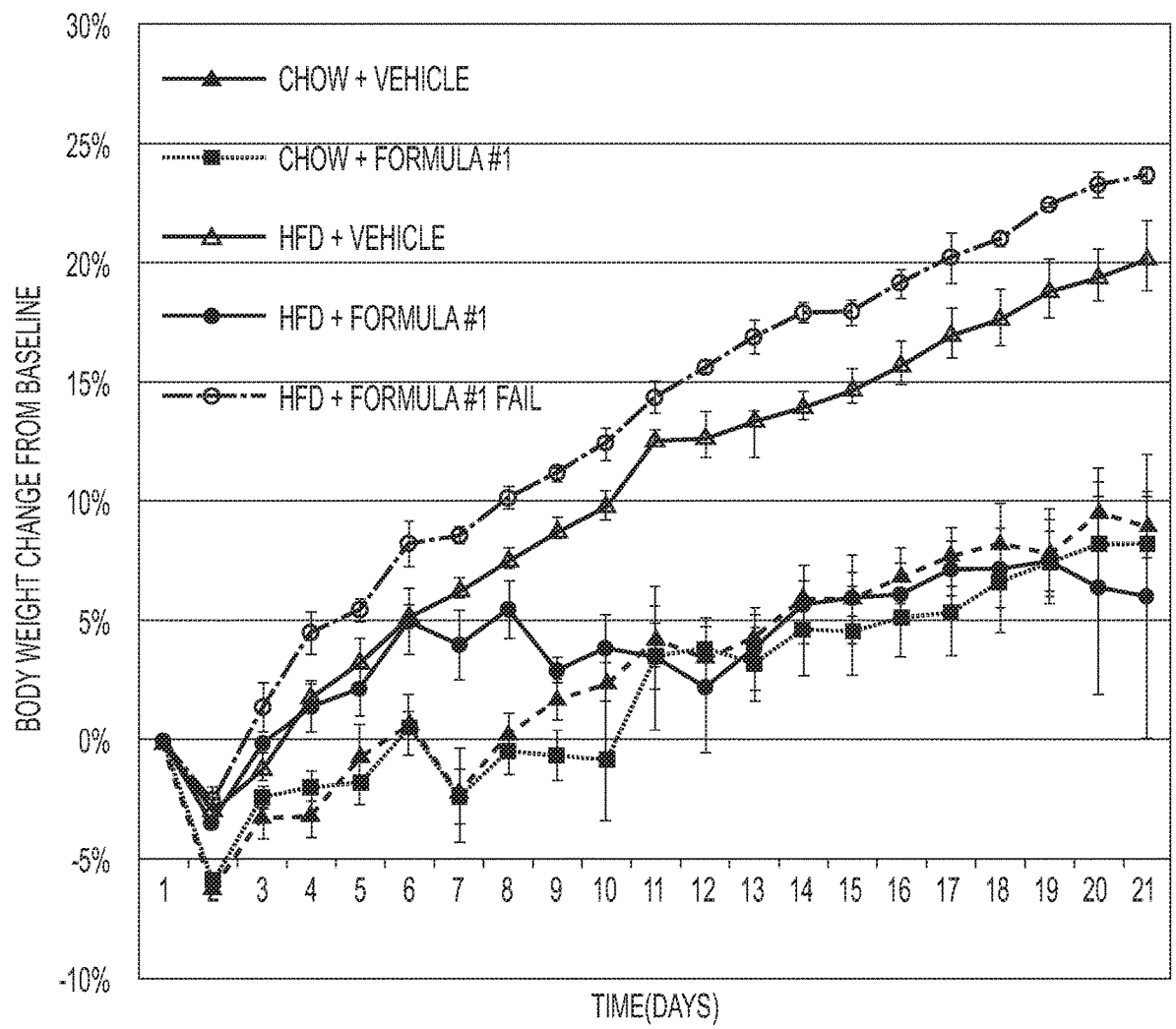
FIG. 5 shows body weight timecourses for rats.

A rodent model of obesity was used to further evaluate the efficacy of Formula 1. Sprague-Dawley male (12 weeks old) rats that were fed either normal chow or a HFD, and animals were treated daily by gavage with either Formula 1 (pH 7 Formulation) or vehicle controls. There were 6 animals in each of the four treatment groups (i.e., chow+vehicle, chow+FORMULA 1, HFD+vehicle, HFD+FORMULA 1). FORMULA 1 treatment dose was 33 mg/kg, which is approximately ~⅓ of the no-observable-adverse-effect-level (NOAEL; 81-115 mg/kg/day) for sodium percarbonate based on chronic oral hydrogen peroxide treatment in rat. (21) Animals treated with FORMULA 1 gained the same amount of weight as did the chow+vehicle control group, while the HFD+vehicle group gained significantly more weight than the others at 21 days (20% vs. 6-9%). A large variability in animals dosed with FORMULA 1 on HFD in terms of efficacy was, however, noted. Half (n=3) of the animals showed strong efficacy while the other half (n=3) of the rats did not; therefore, this latter subgroup is separated out into their own group ("fail group") in the results of this study presented in FIG. 5. Without wishing to be bound by any theory, it is presently believed that the lack of response in this group is due to the un-optimized nature of the pH 7 Formulation for rat physiology. Among other GI differences from human, rats have a lower pH in the intestine (upper range ~5-7) compared to human (upper range ~6.5-7.4) (22) and thus it is believed that the pH 7 Formulation used in this study failed to release API consistently in all the rats due to inter-rat variability at the upper normal range of intestinal pH (i.e., not all rats had a pH of 7 in their intestines). Hence, the stark binary outcome data in the FORMULA 1 high fat dosing group may reflect the variation of API delivery success, due to the specific physiological characteristics of the rat GI tract (pH, transit time, water content etc.).

Variability in intestinal pH aside, the results of this study are consistent with the high efficacy that the API displayed in humans. Similarly, RYGB surgery performed in rat models prevents weight gain in HFD fed animals, but has no effect on body weight in lean, chow fed animals. It can be hypothesized that the stark nature of this binary outcome result in rats (high efficacy in half, no efficacy in the other half) reflects a failure of the formulation (unoptimized coating for the rat intestine), instead of a more graded result (i.e. normal distribution), which would be expected from true physiological variation in response to the encapsulated API. It is also salient to point out that even if the efficacy rates observed with Formula 1 in rats were to translate exactly to humans in large trials, this invention would still become an extremely successful commercial product, as almost all medicines—including surgery (RYGB)—have large efficacy variation in human populations, and there are currently no effective weight loss agents that can achieve efficacy rates on par RYGB.

REFERENCES

1. A. Mor, L. Sharp, D. Portenier, R. Sudan, A. Torquati, Weight loss at first postoperative visit predicts long-term outcome of Roux-en-Y gastric bypass using Duke weight loss surgery chart., *Surg Obes Relat Dis* 8, 556-60 (2012).

2. C. Ciangura, J.-L. L. Bouillot, C. Lloret-Linares, C. Poitou, N. Veyrie, A. Basdevant, J.-M. M. Oppert, Dynamics of change in total and regional body composition after gastric bypass in obese patients., *Obesity (Silver Spring)* 18, 760-5 (2010).

3. A. Flint, A. Raben, J. E. Blundell, A. Astrup, Reproducibility, power and validity of visual analogue scales in assessment of appetite sensations in single test meal studies., *Int. J. Obes. Relat. Metab. Disord.* 24, 38-48 (2000).

4. N. Friedrich, K. Budde, T. Wolf, A. Jungnickel, A. Grotevendt, M. Dressler, H. Völzke, M. Blither, M. Nauck, T. Lohmann, H. Wallaschofksi, Short-term changes of the urine metabolome after bariatric surgery., *OMICS* 16, 612-20 (2012).

5. E. Gralka, C. Luchinat, L. Tenori, B. Ernst, M. Thurnheer, B. Schultes, Metabolomic fingerprint of severe obesity is dynamically affected by bariatric surgery in a procedure-dependent manner., *Am. J. Clin. Nutr.* 102, 1313-22 (2015).

6. J. C. Swaner, W. E. Connor, Hypercholesterolemia of total starvation: its mechanism via tissue mobilization of cholesterol., *Am. J. Physiol.* 229, 365-9 (1975).

7. L. Sävendahl, L. E. Underwood, Fasting increases serum total cholesterol, LDL cholesterol and apolipoprotein B in healthy, nonobese humans., *J. Nutr.* 129, 2005-8 (1999).

8. M. D. Jensen, M. Caruso, V. Heiling, J. M. Miles, Insulin regulation of lipolysis in nondiabetic and IDDM subjects., *Diabetes* 38, 1595-601 (1989).

9. L. P. Palaniappan, Heterogeneity in the Relationship Between Ethnicity, BMI, and Fasting Insulin, *DIABETES CARE* 25 (2002).

10. K. Wickremesekera, G. Miller, T. D. Naotunne, G. Knowles, R. S. Stubbs, Loss of insulin resistance after Roux-en-Y gastric bypass surgery: a time course study., *Obes Surg* 15, 474-81 (2005).

11. A. P. Chambers, L. Jessen, K. K. Ryan, S. Sisley, H. E. Wilson-Pérez, M. A. Stefater, S. G. Gaitonde, J. E. Sorrell, M. Toure, J. Berger, D. A. D'Alessio, S. C. Woods, R. J. Seeley, D. A. Sandoval, Weight-independent changes in blood glucose homeostasis after gastric bypass or vertical sleeve gastrectomy in rats., *Gastroenterology* 141, 950-8 (2011).

12. T. C. Crowe, Safety of low-carbohydrate diets., *Obes Rev* 6, 235-45 (2005).

13. D. W. Foster, J. D. McGarry, The regulation of ketogenesis., *Ciba Found. Symp.* 87, 120-31 (1982).

14. Friedrich N, Budde K, Wolf T, et al. Short-term changes of the urine metabolome after bariatric surgery. OMICS 2012; 16:612-20.

15. Gralka E, Luchinat C, Tenori L, Ernst B, Thurnheer M, Schultes B. Metabolomic fingerprint of severe obesity is dynamically affected by bariatric surgery in a procedure-dependent manner. Am J Clin Nutr 2015; 102:1313-22.

16. Swaner J C, Connor W E. Hypercholesterolemia of total starvation: its mechanism via tissue mobilization of cholesterol. Am J Physiol 1975; 229:365-9.

17. Savendahl L, Underwood L E. Fasting increases serum total cholesterol, LDL cholesterol and apolipoprotein B in healthy, nonobese humans. J Nutr 1999; 129:2005-8.

18. Jensen M D, Caruso M, Heiling V, Miles J M. Insulin regulation of lipolysis in nondiabetic and IDDM subjects. Diabetes 1989; 38:1595-601.

19. Wickremesekera K, Miller G, Naotunne T D, Knowles G, Stubbs R S. Loss of insulin resistance after Roux-en-Y gastric bypass surgery: a time course study. Obes Surg 2005; 15:474-81.

20. Chambers A P, Jessen L, Ryan K K, et al. Weight-independent changes in blood glucose homeostasis after gastric bypass or vertical sleeve gastrectomy in rats. Gastroenterology 2011; 141:950-8.

21. OECD. SODIUM PERCARBONATE. In: Organisation for Economic Co-operation and Development (OECD).

22. Peters S A. Physiologically-Based Pharmacokinetic (PBPK) Modeling and Simulations: Principles, Methods, and Applications in the Pharmaceutical Industry, First Edition. John Wiley & Sons, Inc.; 2012.

The invention claimed is:

1. A method of reducing weight or treating a weight-related condition, the method comprising administering to a subject in need thereof a composition comprising:
A) a plurality of particles, each particle comprising:
 1) a core comprising at least one agent that reacts to release oxygen, and
 2) a delayed release coating encasing the core; and
B) a capsule or sachet encasing the plurality of particles;
wherein the at least one agent is selected from sodium percarbonate and carbamide peroxide.

2. The method of claim 1, wherein the particles further comprise a release rate modifier.

3. The method of claim 1, wherein the particles further comprise a subcoat layer that encases the core and is disposed between the core and the delayed release coating.

4. The method of claim 1, wherein the weight ratio of the delayed release coating to the core of the particles is from 5% to 50%.

5. The method of claim 1, wherein the delayed release coating is an enteric coating that is protective at pH below 5.5.

6. The method of claim 5, wherein the enteric coating is protective at pH below 6.5.

7. The method of claim 5, wherein the enteric coating is protective at pH below 7.0.

8. The method of claim 5, wherein the enteric coating is protective at pH below 7.4.

9. The method of claim 1, wherein the cores of the plurality of particles have a maximum dimension of from 0.1 to 2 mm.

10. The method of claim 1, wherein the particles of the plurality of particles have a maximum dimension of 3.0 mm or less.

11. The method of claim 1, wherein the composition comprises from 25 to 500 mg of the agent.

12. The method of claim 1, wherein the weight reduction comprises at least one of weight loss, maintenance of weight loss, avoiding weight gain, body mass index (BMI) reduction, maintenance of BMI reduction, and avoiding BMI gain.

13. The method claim 1, wherein the subject is overweight or obese.

14. The method of claim 1, wherein the subject has at least one weight-related condition.

15. The method of claim 14, wherein the at least one weight-related condition is selected from a metabolic disease or disorder, metabolic syndrome, and cardiovascular disease.

16. The method of claim 1, wherein administering the composition to the subject increases the relative abundance of at least one of aerobic bacteria and facultatively anaerobic bacteria in the microbiota of the colon of the subject by at least 100%.

17. The method of claim 1, wherein administering the composition to the subject increases the relative abundance of bacteria in at least one phylum selected from Proteobacteria, Bacteriodetes, and Verrucomicrobia in the microbiota of the colon of the subject by at least 100%.

18. The method of claim 1, wherein administering the composition to the subject decreases the relative abundance of bacteria in the Firmicutes phylum in the microbiota of the colon of the subject.

19. The method of claim 1, wherein the composition is characterized in that it achieves release of oxygen when assayed in PBS buffer at pH 7.4 after immersion at pH 1.2 for 2 hours.

20. The method of claim 14, wherein the at least one weight-related condition is selected from selected from hypertension, dyslipidemia, and type 2 diabetes.

21. A method of reducing weight or treating a weight-related condition, the method comprising administering to a subject in need thereof a composition comprising a plurality of particles, each particle comprising:
A) a core comprising at least one agent that reacts to release oxygen, and
B) a delayed release coating encasing the core;
wherein the at least one agent is selected from sodium percarbonate and carbamide peroxide.

22. A method of treating type 2 diabetes, the method comprising administering to a subject in need thereof a composition comprising:
A) a plurality of particles, each particle comprising:
 1) a core comprising at least one agent that reacts to release oxygen, and
 2) a delayed release coating encasing the core; and
B) a capsule or sachet encasing the plurality of particles;
wherein the at least one agent is selected from sodium percarbonate and carbamide peroxide.

23. A method of treating type 2 diabetes, the method comprising administering to a subject in need thereof a composition comprising a plurality of particles, each particle comprising:
A) a core comprising at least one agent that reacts to release oxygen, and
B) a delayed release coating encasing the core;
wherein the at least one agent is selected from sodium percarbonate and carbamide peroxide.

24. The method of claim 21, 22, or 23, wherein the particles further comprise a release rate modifier.

25. The method of claim 21, 22, or 23, wherein the particles further comprise a subcoat layer that encases the core and is disposed between the core and the delayed release coating.

26. The method of claim 21, 22, or 23, wherein the weight ratio of the delayed release coating to the core of the particles is from 5% to 50%.

27. The method of claim 21, 22, or 23, wherein the delayed release coating is an enteric coating that is protective at pH below 5.5.

28. The method of claim 27, wherein the enteric coating is protective at pH below 6.5.

29. The method of claim 27, wherein the enteric coating is protective at pH below 7.0.

30. The method of claim 27, wherein the enteric coating is protective at pH below 7.4.

31. The method of claim 21, 22, or 23, wherein the cores of the plurality of particles have a maximum dimension of from 0.1 to 2 mm.

32. The method of claim 21, 22, or 23, wherein the particles of the plurality of particles have a maximum dimension of 3.0 mm or less.

33. The method of claim 21, 22, or 23, wherein the composition comprises from 25 to 500 mg of the agent.

34. The method of claim 21, wherein the weight reduction comprises at least one of weight loss, maintenance of weight loss, avoiding weight gain, body mass index (BMI) reduction, maintenance of BMI reduction, and avoiding BMI gain.

35. The method claim 21, 22, or 23, wherein the subject is overweight or obese.

36. The method of claim 21, wherein the subject has at least one weight-related condition.

37. The method of claim 36, wherein the at least one weight-related condition is selected from a metabolic disease or disorder, metabolic syndrome, and cardiovascular disease.

38. The method of claim 21, 22, or 23, wherein administering the composition to the subject increases the relative abundance of at least one of aerobic bacteria and facultatively anaerobic bacteria in the microbiota of the colon of the subject by at least 100%.

39. The method of claim 21, 22, or 23, wherein administering the composition to the subject increases the relative abundance of bacteria in at least one phylum selected from Proteobacteria, Bacteriodetes, and Verrucomicrobia in the microbiota of the colon of the subject by at least 100%.

40. The method of claim 21, 22, or 23, wherein administering the composition to the subject decreases the relative abundance of bacteria in the Firmicutes phylum in the microbiota of the colon of the subject.

41. The method of claim 21, 22, or 23, wherein the composition is characterized in that it achieves release of oxygen when assayed in PBS buffer at pH 7.4 after immersion at pH 1.2 for 2 hours.

42. The method of claim 36, wherein the at least one weight-related condition is selected from selected from hypertension, dyslipidemia, and type 2 diabetes.

43. The method of claim 1, 21, 22, or 23, wherein the delayed release coating is an enteric coating.

* * * * *